(12) United States Patent
Tinsley

(10) Patent No.: US 7,521,194 B2
(45) Date of Patent: Apr. 21, 2009

(54) METHOD FOR DETECTION OF MIP-4 AND CCRL2 BINDING AND ACTIVITY MODULATING AGENTS

(75) Inventor: Jonathon Mark Tinsley, Abingdon (GB)

(73) Assignee: Oxagen Limited, Abingdon, Oxfordshire (GB)

( * ) Notice: Subject to any disclaimer, the term of this patent is extended or adjusted under 35 U.S.C. 154(b) by 0 days.

(21) Appl. No.: 10/579,386

(22) PCT Filed: Dec. 2, 2004

(86) PCT No.: PCT/GB2004/005057

§ 371 (c)(1),
(2), (4) Date: May 15, 2006

(87) PCT Pub. No.: WO2005/057220

PCT Pub. Date: Jun. 23, 2005

(65) Prior Publication Data

US 2007/0036781 A1    Feb. 15, 2007

(30) Foreign Application Priority Data

Dec. 5, 2003 (GB) ................................. 0328275.3
Feb. 11, 2004 (GB) ................................. 0403014.4
Aug. 19, 2004 (GB) ................................. 0418568.2

(51) Int. Cl.
*G01N 33/68* (2006.01)
*G01N 33/53* (2006.01)

(52) U.S. Cl. ........................ 435/7.1; 435/7.2; 435/7.31

(58) Field of Classification Search ........................ None
See application file for complete search history.

(56) References Cited

FOREIGN PATENT DOCUMENTS

| WO | WO 95/17092 | 6/1995 |
|---|---|---|
| WO | 96/34891 | 11/1996 |
| WO | 98/01557 | 1/1998 |
| WO | WO 01/66598 A2 | 9/2001 |
| WO | WO 02/22856 A2 | 3/2002 |
| WO | 02/057779 | 7/2002 |
| WO | 2004/045525 | 6/2004 |
| WO | 2004/083232 | 9/2004 |

OTHER PUBLICATIONS

Biber et al. "Expression of L-CCR in HEK 293 cells reveals functional responses to CCL2, CCL5, CCL7, and CCL8" J. Leuk. Biol. 74:243-251 (2003).

Fan et al. "Cloning and characterization of a novel human chemokine receptor" Biochem. Biophys. Res. Comm. 243:264-268 (1998).

Goebeler et al. "Differential and sequential expression of multiple chemokines during elicitation of allergic contact hypersensitivity" Am. J. Pathol. 158:431-440 (2001).

Migeotte et al. "Distribution and regulation of expression of the putative human chemokine receptor HCR in leukocyte populations" Eur. J. Immunol. 32:494-501 (2002).

Mueller et al. "Pharmacological characterization of the chemokine receptor, CCR5" Brit. J. Pharmacol. 135:1033-1043 (2002).

Nibbs et al. "C-C chemokine receptor 3 antagonism by the β-chemokine macrophage inflammatory protein 4, a property strongly enhanced by an amino-terminal alanine-methionine swap" J. Immunol. 164:1488-1497 (2000).

Ogilvie et al. "Eotaxin is a natural antagonist for CCR2 and an agonist for CCR5" Blood 97:1920-1924 (2001).

Pardo et al. abstract of "CCL18/DC-CK-1/PARC up-regulation in hypersensitivity pneumonitis" J. Leuk. Biol. 70:610-616 (2001).

Schutyser et al. "Selective induction of CCL18/PARC by staphylococcal enterotoxins in mononuclear cells and enhanced levels in septic and rheumatoid arthritis" Eur. J. Immunol. 31:3755-3762 (2001).

Smith et al. "CCL18/DC-CK-1/PARC up-regulation in hypersensitivity pneumonitis" J. Leukoc. Biol. 70:610-616 (2001).

Weisberg et al. "Obesity is associated with macrophage accumulation in adipose tissue" J. Clin. Invest. 112:1796-1808 (2003).

Xu et al. "Chronic inflammation in fat plays a crucial role in the development of obesity-related insulin resistance" J. Clin. Invest. 112:1821-1830 (2003).

Zuurman et al. "LPS-induced expression of anovel chemonkine receptor (L-CCR) in mouse glial cells in vitro and in vivo" Glia 41:327-336 (2003).

International Preliminary Report on Patentability for Appln. No. PCT/GB2004/005057 dated Jun. 15, 2006.

International Search Report for PCT/GB04/05057 dated Nov. 7, 2005.

Galligan et al., "Up-regulated expression and activation of the orphan chemokine receptor, CCRL2, in rheumatoid arthritis" *Arthritis & Rheumatism*, vol. 50, No. 6, pp. 1806-1814, Jun. 2004, XP002349008.

Pardo et al. "CCL18/DC-CK-1/PARC up-regulation in hypersensitivity pneumonitis" J. Leukocyte Biol. 70:610-616 (2001).

(Continued)

*Primary Examiner*—Elly-Gerald Stoica
(74) *Attorney, Agent, or Firm*—Nixon & Vanderhye P.C.

(57) ABSTRACT

A method of detecting an agent that modulates the activity of CCRL2, the method comprising: (a) contacting a CCRL2 polypeptide with a macrophage inflammatory protein-4 (MIP-4) polypeptide in the presence of a candidate agent under conditions, which in the absence of the test agent, permit the binding of the MIP-4 polypeptide to the CCRL2 polypeptide; and (b) determining whether the candidate agent is capable of modulating the interaction between said CCRL2 polypeptide and said MIP-4 polypeptide.

19 Claims, 6 Drawing Sheets

METHOD FOR DETECTION OF MIP-4 AND CCRL2 BINDING AND ACTIVITY MODULATING AGENTS

This application is a U.S. national stage of International Patent Application No. PCT/GB2004/005057, filed 2 Dec. 2004, which designated the U.S. and claims priority of GB 0328275.3, filed 5 Dec. 2003; GB 0403014.4, filed 11 Feb. 2004; and GB 0418568.2, filed 19 Aug. 2004; the entire contents of each of which are hereby incorporated by reference.

FIELD OF THE INVENTION

The present invention relates to an endogenous ligand for an orphan G protein coupled receptor and to associated methods, uses, agents, compositions and kits.

BACKGROUND OF THE INVENTION

Chemokines acting through their cognate receptors are critical for the recruitment of effector immune cells to inflamed tissues, and are therefore of considerable interest as potential targets for the treatment of inflammatory disease. CCRL2 (also known as HCR, CRAM-A and CRAM-B) encodes an orphan chemokine receptor-like protein, which is predicted to be a seven transmembrane protein. G protein coupled receptors (GPCRs) are a family of approximately 500 proteins with a 7 transmembrane structure that transduce cellular signals of a variety of biological mediators. The interaction of a GPCR and its ligand causes a conformational change in the protein and facilitates the binding of small associated heterotrimeric G proteins to the intracellular receptor domains, which initiate a signalling cascade. GPCRs are cell surface receptors and therefore are attractive targets for pharmacological intervention. CCRL2 is expressed at high levels in primary neutrophils and primary monocytes, and is further upregulated on neutrophil activation and when monocytes differentiate to macrophages. However, the importance of CCRL2 in human inflammatory disease has not been investigated.

SUMMARY OF THE INVENTION

The present inventors have identified macrophage inflammatory protein-4 (MIP-4; also known as DC-CKI, CCL18 and PARC) as an endogenous ligand for CCRL2.

Accordingly, the present invention provides a method of detecting an agent that modulates the activity of CCRL2, the method comprising:

(a) contacting a CCRL2 polypeptide with a macrophage inflammatory protein-4 (MIP-4) polypeptide in the presence of a candidate agent under conditions, which in the absence of the test agent, permit the binding of the MIP-4 polypeptide to the CCRL2 polypeptide; and (b) determining whether the candidate agent is capable of modulating the interaction between said CCRL2 polypeptide and said MIP-4 polypeptide.

The present invention further provides:

an agent detected by a method of the invention;
an antibody specific for MIP-4, which antibody is capable of inhibiting binding of MIP-4 to CCRL2;
an antibody specific for CCRL2, which antibody is capable of inhibiting binding of CCRL2 to MIP-4;
a method of modulating the activating of a CCRL2 polypeptide in a cell, the method comprising delivering an agent according to the invention to the cell;
a pharmaceutical composition comprising an agent according to the invention and a pharmaceutically acceptable carrier or diluent;
a method for treating an inflammatory disease or disorder in an individual, the method comprising administering a therapeutically effective amount of an agent according to the invention or a pharmaceutical composition according to the invention to the individual;
a method for treating a disease or disorder associated with enhanced macrophage activity in an individual, the method comprising administering a therapeutically effective amount of an agent according to the invention or a pharmaceutical composition according to the invention to the individual;
an agent according to the invention or a pharmaceutical composition according to the invention for use in a method of treatment of a human or animal body or therapy;
use of an agent according to the invention in the manufacture of a medicament for the treatment of an inflammatory disease or disorder;
use of an agent according to the invention in the manufacture of a medicament for the treatment of a disease or disorder associated with enhanced macrophage activity,
a method of activating a CCRL2 signalling pathway in a cell, the method comprising delivering, to the cell, a polypeptide comprising:
  (a) the MIP-4 sequence shown in SEQ ID NO: 6; or
  (b) a sequence at least 50% identical to SEQ ID NO: 6 and which binds to and activates a signalling activity of CCRL2;
or a fragment of SEQ ID NO: 6 which binds to and activates a signalling activity of CCRL2;
use of a polypeptide comprising:
  (a) the MIP-4 sequence shown in SEQ ID NO: 6; or
  (b) a sequence at least 50% identical to SEQ ID NO: 6 and which binds to and activates a signalling activity of CCRL2; or
  (c) a fragment of SEQ ID NO: 6 which binds to and activates a signalling activity of CCRL2;
a polynucleotide encoding any of said polypeptides or said fragments or an antibody specific for any of said polypeptides or said fragments; for the manufacture of a medicament for treating a CCRL2-related disease or disorder;
use of a polypeptide comprising:
  (a) the CCRL2 sequence shown in SEQ ID NO: 2 or 4; or
  (b) a sequence which is at least 80% identical to SEQ ID NO: 2 or 4 over its entire length and functionally equivalent to CCRL2; or
  (c) a fragment of SEQ ID NO: 2 or 4 which is functionally equivalent to CCRL2,
a polynucleotide encoding any of said polypeptides, or an antibody which binds to any of said polypeptides; for the manufacture of a medicament for treating a MIP-4-related disease or disorder;
a method of diagnosing a CCRL2-related disease or disorder in an individual, the method comprising:
  (a) carrying out an amplification reaction on a sample isolated from the individual using primers specific for a polynucleotide encoding a MIP-4 polypeptide; and
  (b) determining the presence or absence of a polynucleotide encoding a MIP-4 polypeptide in the sample and thereby determining the presence of a CCRL2-related disease or disorder in the individual;
a method of diagnosing a CCRL2-related disease or disorder in an individual, the method comprising:

(a) amplifying a polynucleotide encoding a MIP-4 polypeptide, using a nucleic acid isolated from the individual; and (b) determining whether the polynucleotide comprises a polymorphism associated with a CCRL2 related disease or disorder; and (c) determining on the basis of said comparison whether the polynucleotide comprises a polymorphism associated with a CCRL2-related disease or disorder.

a method of diagnosing a CCRL2-related disease or disorder in an individual, the method comprising:

(a) contacting a sample isolated from the individual comprising a CCRL2 polypeptide with a MIP-4 polypeptide under conditions which permit the binding of the MIP-4 polypeptide to the CCRL2 polypeptide;

(b) measuring the activity of the CCRL2 polypeptide; and (a) comparing the activity of the CCRL2 polypeptide with a standard, wherein a difference in the activity relative to the standard is indicative of the presence of a CCRL2-related disease or disorder in the individual;

a kit for detecting an agent that modulates the activity of CCRL2, the kit comprising: (i) a CCRL2 polypeptide or a polynucleotide encoding a CCRL2 polypeptide.

DESCRIPTION OF THE SEQUENCES MENTIONED HEREIN

SEQ ID NO: 1 shows the polynucleotide that encodes the long form of human CCRL2 (CRAM-A).

SEQ ID NO: 2 shows the amino acid sequence of the long form of human CCRL2 (CRAM-A).

SEQ ID NO: 3 shows the polynucleotide that encodes the short form of human CCRL2 (CRAM-B).

SEQ ID NO: 4 shows the amino acid sequence of the short form of human CCRL2 (CRAM-B).

SEQ ID NO: 5 shows the polynucleotide that encodes human MIP-4.

SEQ ID NO: 6 shows the amino acid sequence of human MIP-4.

DETAILED DESCRIPTION OF THE INVENTION

Figure 1:
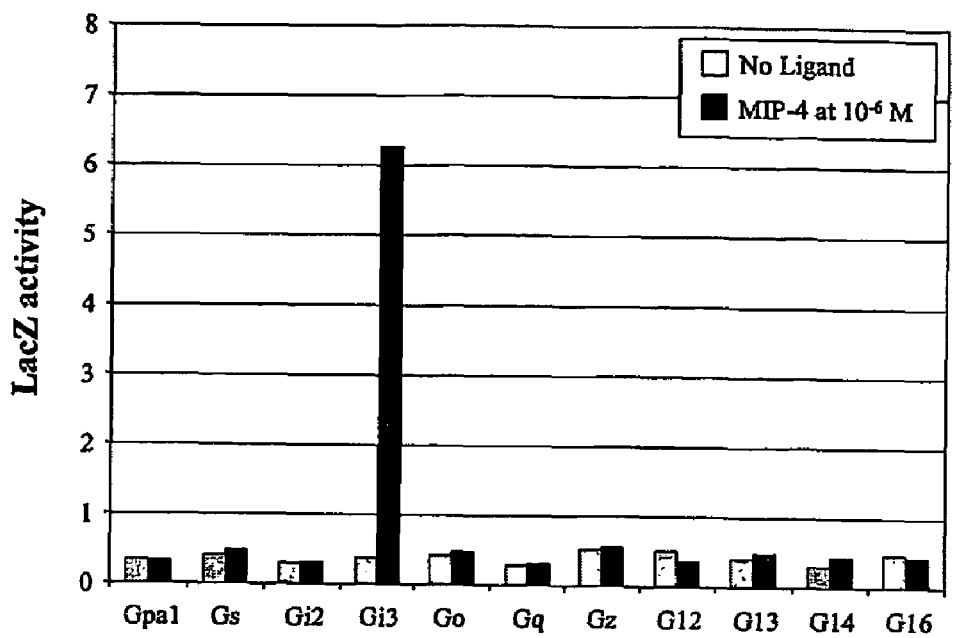
FIG. 1 shows LacZ activity in G-protein transplant yeast cells in the presence and absence of MIP-4. LacZ activity is expressed per $10^6$ cells.

It is to be understood that different applications of the disclosed methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polypeptide" includes a mixture of two or more such polypeptides, reference to "a cell" includes two or more such cells, and the like.

All publications, patents and patent applications cited herein, whether supra or infra, are hereby incorporated by reference in their entirety.

Screening for Agents that Modulate the Activity of CCRL2

The invention provides a method of detecting a candidate agent that modulates the activity of CCRL2. The term "modulate" includes any of the ways mentioned herein in which the agent of the invention is able to modulate CCRL2. This includes upregulation or downregulation of CCRL2 expression, upregulation or downregulation of CCRL2 degradation, stimulation or inhibition of CCRL2 receptor activity, including potentiation of CCRL2 activity in response to a MIP-4 polypeptide. The ability of a candidate agent to modulate the activity or expression of CCRL2 may be determined by contacting a CCRL2 polypeptide with the agent under conditions that, in the absence of the candidate agent, permit activity or expression of CCRL2, for example in the presence of a MIP-4 polypeptide, and comparing CCRL2 activity in the presence and absence of the candidate agent. Preferably, the modulation is a correction of aberrant CCRL2 activity or expression. CCRL2 activity is typically activation of a G-protein mediated signalling pathway. The G-protein may be any G-protein that is coupled to the CCRL2 polypeptide. Preferably the G-protein is Gi3.

The methods of detecting an agent that modulates the activity of a CCRL2 polypeptide may be carried out in vitro (inside or outside a cell) or in vivo. In one embodiment the methods are carried out in or on a cell, cell culture or cell extract which comprises a CCRL2 polypeptide or expresses a CCRL2 polynucleotide. The cell may be one in which the CCRL2 polypeptide is naturally expressed, such as an endothelial cell. Alternatively, the cell may be a cell that is transformed with a CCRL2 polynucleotide and expresses a CCRL2 polypeptide. Suitable cells include transient, or preferably stable higher eukaryotic cell lines, such as mammalian cells or insect cells, lower eukaryotic cells, such as yeast, or prokaryotic cells such as bacterial cells. Particular examples of cell lines include mammalian HEK293T, CHO, HeLa and COS cells. Preferably the cell line selected will be one which is not only stable, but also allows for mature glycosylation of a polypeptide. Expression of a CCRL2 polypeptide may also be achieved in transformed oocytes.

In another embodiment, the methods are carried out in or on a liposome comprising a CCRL2 polypeptide. Methods for the preparation of liposomes are well known in the art (Woodle and Papahadjopoulos, Methods Enzymol., 1989; 171: 193-217).

In a further embodiment, the methods are carried out in or on virus-induced budding membranes comprising a CCRL2 polypeptide. Methods for the preparation of virus-induced budding membranes are well known in the art (for example, Luan et al., Biochemistry, 1995; 34(31): 9874-9883). Viruses may be used to induce budding in cells expressing a CCRL2 polypeptide naturally or cells transformed (transfected) with a CCRL2 polynucleotide.

In a further embodiment, the methods are carried out in or on artificial lipid bilayers. Methods for the preparation of artificial lipid bilayers are well known in the art (Sackmann and Tanaka, Trends Biotechnol., 2000; 18: 58-64; and Karlsson and Lofas, Anal. Biochem., 2002; 300: 132-138). A CCRL2 polypeptide may be integrated into the artificial membrane when the membrane is fabricated.

In a yet further embodiment, the methods are carried out in or on a membrane fraction comprising the CCRL2 polypeptide. A membrane fraction is a preparation of cellular lipid membranes in which some, for example at least 5% or 10%, of the non-membrane-associated elements have been removed. Membrane-associated elements are cellular constituents that are integrated into the lipid membrane or cellular constituents physically associated with a component integrated into the lipid membrane. Methods for the preparation of cellular membrane fractions are well known in the art (for example, Hubbard and Cohn, 1975, J. Cell. Biol., 64; 461-479). A membrane fraction comprising the CCRL2 polypeptide may be prepared from cells expressing a CCRL2 polypeptide naturally or cell transformed (transfected) with a CCRL2 polynucleotide. Alternatively, a CCRL2 polypeptide may be integrated into a membrane preparation by dilution of a detergent solution of the CCRL2 polypeptide (for example, Salamon et al., 1996, Biophys. J., 71: 283-294).

The methods for identifying an agent that modulates the activity of a CCRL2 polypeptide are carried out using a candidate agent. The method typically comprises using one or more candidate agents, for example 1, 2, 3, 4, 5, 10, 15, 20 or 30 or more candidate agents. A candidate agent is a candidate compound being evaluated for the ability to modulate the activity of CCRL2 by the methods of the invention. Candidate agents can be natural or synthetic compounds, including, for example, small molecules, compounds contained in extracts of animal, plant, bacterial or fungal cells, as well as conditioned medium from such cells. Suitable candidate agents which may be tested in the above screening methods include antibody agents (for example, monoclonal and polyclonal antibodies, single chain antibodies, chimeric antibodies and CDR-grafted antibodies) or aptamer agents. The antibody agent may have binding affinity for the CCRL2 receptor or for a MIP-4 polypeptide. Furthermore, combinatorial libraries, defined chemical identities, peptide and peptide mimetics, oligonucleotides and natural agent libraries, such as display libraries (e.g. phage display libraries) may also be tested. Oligonucleotide libraries, such as aptamer libraries may be tested.

The candidate agents may be chemical compounds, which are typically derived from synthesis around small molecules which may have any of the properties of the MIP-4 polypeptide.

The candidate agent may be derived from or contained in an environmental sample, a natural extract of animal, insect, marine organism, plant, yeast or bacterial cells or tissues, a clinical sample, a synthetic sample, or a conditioned medium from recombinant cells or a fermentation process. The candidate agent may also be derived from or contained in a tissue sample which comprises a body fluid and/or cells of an individual and may, for example, be obtained using a swab, such as a mouth swab. The candidate agent may be derived from or contained in a blood, urine, saliva, skin, cheek cell or hair root sample.

Batches of the candidate agents may be used in an initial screen of, for example, ten candidate agents per reaction, and the candidate agents of batches which show modulation tested individually. Where a batch of agents shows CCRL2 modulatory activity the test agents may be tested in smaller batched or individually to identify the agent having modulatory activity.

Preferred candidate agents are polypeptides, antibodies or antigen-binding fragments thereof, lipids, carbohydrates, nucleic acids and chemical compounds.

The methods of the invention detect agents that modulate the activity of a CCRL2 polypeptide by determining or assaying the effect of a candidate agent on an activity of the CCRL2 polypeptide such as ligand binding, signalling activity or chemotactic activity. The methods of the invention are carried out under conditions which, in the absence of the candidate agent, permit the binding of a MIP-4 polypeptide to a CCRL2 polypeptide. These conditions are, for example, the temperature, salt concentration, pH and protein concentration under which a MIP-4 polypeptide binds to a CCRL2 polypeptide. Exact binding conditions will vary depending upon the nature of the assay, for example, whether the assay uses viable cells or only membrane fraction of cells. However, because CCRL2 is a cell surface receptor and MIP-4 polypeptides are secreted polypeptides that interact with the extracellular domain of CCRL2, preferred conditions will generally include physiological salt concentration (approximately 90 mM) and pH (about 7.0 to 8.0). Temperatures for binding may vary from 4° C. to 37° C., but is preferably 4° C. The concentration of reactants in the binding assay will also vary, but will preferably be from about 0.1 pM to about 10 μM.

In one embodiment of the invention, the effect of the test sample on the binding of the CCRL2 polypeptide to a MIP-4 polypeptide is monitored. Any suitable binding assay format can be used to monitor binding and detect any effect. The effect may be measured as a decrease in the binding between a MIP-4 polypeptide and a CCRL2 polypeptide. A decrease of at least 10%, at least 20%, at least 30%, at least 40%, at least 50%, at least 60%, at least 70% or at least 80% in the binding between a MIP-4 polypeptide and a CCRL2 polypeptide measured in any given assay indicates that the candidate agent modulates the activity of CCRL2.

Preferred assays for monitoring any candidate agent-induced changes in the binding between a MIP-4 polypeptide and a CCRL2 polypeptide include label displacement, surface plasmon resonance, fluorescence resonance energy transfer, fluorescence quenching, fluorescence polarization and radioligand binding assays.

Label displacement involves contacting a CCRL2 polypeptide with a detectably labelled MIP-4 polypeptide in the presence or absence of increasing concentrations of a candidate agent. To calibrate the assay, control competition reactions using increasing concentrations of an unlabelled MIP-4 polypeptide may be carried out. After contact, bound, labelled MIP-4 polypeptide is measured using a method appropriate for the given label (for example scintillation counting, enzyme assay or fluorescence). Preferred labels include radioisotopes such as tritium or iodine or any other suitable radionucleotide. Candidate agents are considered to bind specifically to a CCRL2 polypeptide if they displace 50% of labelled MIP-4 polypeptide at a concentration of 10 μM or less ($EC_{50}$ is 10 μM or less).

Surface plasmon resonance measures binding between the two molecules by the change in mass near an immobilized sensor caused by the binding or loss of binding of a MIP-4 polypeptide to a CCRL2 polypeptide immobilized in a membrane on the sensor. The change in mass is measured as resonance units versus time after injection or removal of the ligand or candidate agent and is measured using a Biacore Biosensor (Biacore AB). A CCRL2 polypeptide may be immobilized on a sensor chip in a thin film lipid membrane according to methods described (Salamon et al., 1996, Biophys J. 71: 283-294). Generally, a candidate agent may be administered to a MIP-4 polypeptide pre-bound to an immobilized CCRL2 polypeptide and displacement of the ligand measured. Alternatively, a MIP-4 polypeptide may be administered to a candidate agent pre-bound to an immobilized CCRL2 polypeptide.

Fluorescence resonance energy transfer (FRET) is a quantum mechanical phenomenon that occurs between a fluorescence donor (D) and a fluorescence acceptor (A) in close proximity to each other if the emission spectrum of D overlaps with the excitation spectrum of A. Generally, the MIP-4 polypeptide and the CCRL2 polypeptide are labelled with a complementary pair of donor and acceptor fluorophores. The fluorescence emitted upon excitation of the donor fluorophore will have a different wavelength when the MIP-4 polypeptide and CCRL2 polypeptide are bound than when they are not bound. Quantitation of bound versus unbound polypeptides can be carried out by measurement of emission intensity at each wavelength. Donor: Acceptor pairs of fluorophores with which to label the polypeptides are well known in the art. Preferred fluorophores are Cyan Fluorescent Protein (CFP, Donor) and Yellow Fluorescent Protein (YFP, Acceptor).

Fluorescence quenching involves labelling one molecule of the binding pair (MIP-4 polypeptide and CCRL2 polypeptide) with a fluorophore while labelling the other with a molecule that quenches the fluorescence of the fluorophore when the pair bind. A change in fluorescence upon excitation may be used to measure a change in the binding between the MIP-4 polypeptide and CCRL2. An increase in fluorescence suggests that the binding between the MIP-4 polypeptide and CCRL2 polypeptide is decreased.

Fluorescence polarization measures the polarization of a fluorescently-labelled MIP-4 polypeptide. The fluorescence polarization value for a fluorescently-labelled MIP-4 polypeptide will change, and generally increase, when the ligand binds to a CCRL2 polypeptide. A decrease in the polarization value is typically indicative of a decrease in binding between the MIP-4 polypeptide and CCRL2 polypeptide. Fluorescence polarization is preferable when the candidate agent is a small molecule.

Large scale, high throughput screening of small candidate agents or libraries of such agents may be screened using biosensor assays. ICS biosensors have been described by AMBRI (Australian Membrane Biotechnology Research Institute; http//www.ambri.com.au/). The binding of a ligand for CCRL2 to CCRL2 is coupled to the closing of gramacidin-facilitated ion channels in a membrane bilayer of the biosensors. As a result, the biosensor may measure binding between the MIP-4 polypeptide and CCRL2 polypeptide and therefore any changes in binding upon introduction of a candidate agent.

Agents that interfere with or displace binding of a MIP-4 polypeptide from a CCRL2 polypeptide may be agonists, partial agonists, antagonists or inverse agonists of CCRL2 activity. Functional analysis can be performed on agents identified according to the invention to determine whether they are an agonist, partial agonist, antagonist or inverse agonist. For agonist screening, a CCRL2 polypeptide is contacted with agent and the signalling activity of CCRL2 measured as described below. An agonist or partial agonist will have a maximal activity corresponding to at least 10% of the maximal activity of a MIP-4 polypeptide. The agonist or partial agonist will preferably have 50%, 75%, 100% activity of the MIP-4 polypeptide or 2-fold, 5-fold, 10-fold or more activity than a MIP-4 polypeptide. For antagonist or inverse agonist screening, CCRL2 polypeptides are assayed for signalling activity in the presence of a MIP-4 polypeptide, with or without a candidate compound. Antagonists or inverse agonists will reduce the level of ligand-stimulated receptor activity by at least 10%, compared to reactions lacking the antagonist or inverse agonist. For inverse agonist screening, constitutive CCRL2 activity is assayed in the presence and absence of a candidate compound. Inverse agonists are compounds that reduce the constitutive activity of the receptor by at least 10%. Constitutive activity of a CCRL2 polypeptide may be achieved by overexpression by placing, for example, placing it under the control of a strong constitutive promoter such as the CMV early promoter. Alternatively, constitutive activity may be achieved by certain mutations of conserved G-protein coupled receptor amino acids or amino acid domains (for example, Kjelsberg et al., 1992, J. Biol. Chem. 267:1430-1430; Ren et al., 1993, J. Biol. Chem. 268:16483-16487; and Samama et al., 1993, J. Biol. Chem 268:4625-4636).

In another embodiment of the invention, the effect of a test sample on the signalling activity of a CCRL2 polypeptide is monitored. The signalling activity of CCRL2 is induced by a MIP-4 polypeptide. Any suitable signalling assay format may be used for monitoring signalling activity and detecting any effect. The effect may be measured as a change in the MIP-4 polypeptide-induced signalling activity of CCRL2. A change refers to an increase or a decrease in the signalling activity. A change of at least 10%, at least 20%, at least 30%, at least 40%, at least 50%, at least 60%, at least 70% or at least 80% in the signalling activity a CCRL2 polypeptide measured in any given assay indicates that the candidate agent modulates the activity of CCRL2.

The signalling activity of a CCLR2 polypeptide may be monitored by measuring the level of activation of a G protein by the CCLR2 polypeptide. The level of activation of a G protein by CCRL2 may be monitored by measuring the turnover of guanosine derivatives, the activity of guanosine triphosphatase (GTPase) or level of downstream second messenger molecules. Guanosine derivatives are involved in the cyclic reaction of activation and inactivation of G proteins include guanosine diphospahte (GDP) and guanosine triphosphate (GTP). Second messenger molecules are generated or caused to alter in concentration by the activation of a G protein. Examples include but are not limited to cyclic adenine monophosphate (cAMP), cyclic guanosine monophosphate (cGMP), diacylglycerol (DAG), inositol triphosphate ($IP_3$) and intracellular calcium.

Preferred methods of monitoring signalling activity include measuring guanosine nucleotide binding, GTPase activity, adenylate cyclase activity, cAMP, Protein Kinase C activity, phosphatidylinositol breakdown, diacylglycerol, inositol triphosphate, intracellular calcium, MAP kinase activity and reporter gene expression. In all assays, potential non-specific effects of the candidate agent may be excluded by carrying out control assays using cells or membranes that do not comprise a CCRL2 polypeptide.

Preferably, the signalling activity of the CCRL2 polypeptide is monitored by measuring the activity of Gi3.

GTP binds to membrane-associated G proteins upon activation by a receptor such as a CCRL2 polypeptide. CCRL2 signalling activity may therefore be assayed by measuring the binding of GTP to cell membranes containing receptors (Traynor and Nahorski, 1995, Mol. Pharmacol. 47: 848-854).

Generally, GTP is labelled with a suitable detectable moiety and measured by an appropriate detection system.

G proteins comprise a GTPase which hydrolyses GTP to form GDP and inactivates the G protein. GTPase activity is therefore a measure of G protein and therefore CCRL2 activity. GTPase activity may be measured by methods common in the art. Generally, the method involves incubating the membranes containing a CCRL2 polypeptide with γP-GTP. Active GTPase will release the label as inorganic phosphate which may be detected by scintillation counting.

Another preferred method of monitoring signalling activity is measuring adenylate cyclase activity (Solomon et al., 1974, Anal. Biochem. 58: 541-548; and Kenimer & Nirenberg, 1981, Mol. Pharmacol. 20: 585-591). The assay may involve the use of labelled cAMP to estimate the activity of the adenylate cyclase enzyme in protein homogenates from cells or membrane comprising a CCRL2 polypeptide.

A yet further preferred method of monitoring signalling activity is the measurement of intracellular cAMP. This may be done using a cAMP radioimmunoassay (RIA) or cAMP binding proteins according to methods known in the art (Horton & Baxendale, 1995, Methods Mol. Biol. 41: 91-105). Intracellular cAMP may be measured using a number of commercially available kits including the High Efficiency Fluorescence Polarization-based homogeneous assay (LJL Biosystems and NEN Life Science Products).

Yet further preferred methods of monitoring signalling activity measure receptor induced breakdown of phospholipids (especially phosphatidylinositol) to generate the second messengers DAG and/or $IP_3$. Methods of measuring each of these are well known in the art (for example, Phospholipid Signaling Protocols, edited by Ian M. Bird. Totowa, N.J., Humana Press, 1998; and Rudolph et al., 1999, J. Biol. Chem. 274: 11824-11831).

A yet further preferred method of monitoring signalling activity measures receptor induced Protein Kinase C (PKC) activity. DAG activates PKC which phosphorylates many target proteins and ultimately results in the transcription of an array of proto-oncogene transcription factor-encoding genes, including c-fos, c-myc and c-jun, proteases; protease inhibitors, including collagenase type I and plasminogen activator inhibitor; and adhesion molecules, including intracellular adhesion molecule I (ICAM I). The activity of PKC may be measured directly by measuring phosphorylation of a substrate peptide, Ac-FKKSFKL-NH2, which derived from the myristoylated alanine-rich protein kinase C substrate protein (MARCKS) (Kikkawa et al., 1982, J. Biol. Chem. 257: 13341-13348). Assays designed to detect increases in gene products induced by PKC can be used to monitor PKC activation and thereby receptor activity. In addition, the activity of a receptor that activates PKC can be monitored through the use of reporter gene constructs driven by the control sequences of genes activated by PKC activation (see below).

Another preferred method for monitoring signalling activity measures MAP kinase activity. Several kits are commercially available, including the p38 MAP Kinase assay kit (New England Biolabs (Cat #9820)) and the FlashPlate™ MAP Kinase assay (Perkin-Elmer Life Sciences).

Another preferred method for monitoring signalling activity is the measurement of intracellular calcium. Various methods of measuring intracellular calcium are well known in the art (Demaurex et al., Meth. Cell. Biol., 2002; 70: 453-474). Several kits are commercially available for measuring intracellular calcium including the FILPR assay kits (Biocompare, Inc.). One preferred method of measuring intracellular calcium is the aequorin assay. Mitochondrial apoaequorin is a bioluminescent protein that is responsive to intracellular calcium ion release resulting from the activation of GPCRs such as CCRL2 (Stables et al., 1997, Anal. Biochem. 252:115-126; and Detheux et al., 2000, J. Exp. Med., 192 1501-1508). Generally, cells expressing a CCRL2 polypeptide are transfected to coexpress mitochondrial apoaequorin and Gα16. Any compound that activates the CCRL2 polypeptide, such as a MIP-4 polypeptide, will cause intracellular calcium release and result in a light emission that may be measured. A second preferred method of measuring intracellular calcium is the Fura-2 assay (Molecular Probes, Eugene, Oreg. USA).

Other preferred methods of monitoring signalling activity measure changes in the transcription or translation of one or more genes. Generally, assays measure the expression of a reporter gene driven by control sequences, such as promoters and transcription-factor binding sites, responsive to receptor activation. Cells that comprise a CCRL2 polypeptide may be stably transfected with a reporter gene construct containing appropriate control sequences. Assays tend to involve measuring the response of "immediate early" genes which may be rapidly induced, possibly within minutes, of receptor activation. Suitable reporter genes include, but are not limited to, luciferase, CAT, GFP, β-lactamase or β-galactosidase. An example of a control sequence that may be used in a reporter gene assay are those of the c-fos gene. The induction of c-fos expression is extremely rapid, often within minutes, of receptor activation. The c-fos regulatory elements are well known in the art (Verma et al., 1987, Cell 51: 513-514). A further example of a control sequence that may be used in a reporter gene assay are those recognised by CREB (cyclic AMP responsive element binding protein). Other examples of control sequences that may be used in a reporter gene assay include, but are not limited to, the vasoactive intestinal peptide (VIP) gene promoter (Fink et al., 1988, Proc. Natl. Acad. Sci. 85:6662-6666); the somatostatin gene promoter (Montminy et al., 1986, Proc. Natl. Acad. Sci. 83:6682-6686); the proenkephalin promoter (Comb et al., 1986, Nature 323:353-356); the phosphoenolpyruvate carboxy-kinase (PEPCK) gene promoter (Short et al., 1986, J. Biol. Chem. 261:9721-9726); and transcriptional control elements responsive to the AP-1 transcription factor (Lee et al, 1987, Nature 325: 368-372; and Lee et al., 1987, Cell 49: 741-752) or NF-κB activity (Hiscott et al., 1993, Mol. Cell. Biol. 13: 6231-6240). Although for other signalling activity assays, a change of at least 10% in the presence of a candidate agent indicates that it modulates CCRL2, the transcriptional reporter assay requires at least a two-fold increase in signal to indicate the presence of a positive agent. As with other assays, a negative agent is indicated by at a 10% decrease in signal in the reporter gene expression assay.

The ability of a candidate agent identified by a method of the invention to modulate the signalling activity of a CCRL2 polypeptide may be further confirmed or analysed. This functional analysis is described in detail above. This analysis typically involves monitoring of the effect of candidate agent alone on the signalling activity of a CCRL2 polypeptide and comparison with the effect of a MIP-4 polypeptide on the signalling activity of the CCRL2 polypeptide. Any suitable signalling assay format may be used for determining signalling activity and detecting the effect. The effect may be measured as a change in the signalling activity of CCRL2. The agent may be agonist, partial agonist, antagonist or inverse agonist of CCRL2 activity.

Comparisons are made with a MIP-4 polypeptide at its $EC_{50}$. The $EC_{50}$ refers to the concentration of ligand at which the signalling activity is 50% of the maximum for the receptor activity measurable using the same assay. In other words, the $EC_{50}$ is the concentration of ligand that gives 50% activation, when 100% activation is set at the amount of activity that does not increase with the addition of more ligand. It should be noted that the $EC_{50}$ of a ligand will vary with the identity of the ligand, for example, variants of SEQ ID NO: 6 (i.e., those containing insertions, deletions, substitutions) can have $EC_{50}$ values higher than, lower than or the same as the parent molecule. Where a sequence differs from a parent sequence, one of skill in the art can determine the $EC_{50}$ for that variant according to conventional methods. The $EC_{50}$ of a given ligand is measured by performing an assay for an activity of a fixed amount of a CCRL2 polypeptide in the presence of doses of the ligand that increase at least until the CCRL2 response is saturated or maximal, and then plotting the measured CCRL2 activity versus the concentration of the ligand.

The candidate agent is regarded as an agent that modulates CCRL2 activity if it induces at least 50% of the signalling activity induced by a MIPA polypeptide at its $EC_{50}$.

In another embodiment of the invention, the effect of a candidate agent or sample on the chemotactic activity of a CCRL2 polypeptide is monitored. The chemotactic activity of CCRL2 is induced by a MIP-4 polypeptide. Any suitable chemotactic assay format may be used for monitoring chemotactic activity and detecting any effect. A chemotactic assay is a measure of cell migration to a stimulus. The effect may be measured as a change in the MIP-4 polypeptide-induced chemotactic activity of CCRL2. A change refers to an increase or a decrease in the signalling activity. A change of at least 10%, at least 20%, at least 30%, at least 40%, at least 50%, at least 60%, at least 70% or at least 80% in the chemotactic activity of a CCRL2 polypeptide measured in any given assay indicates that the candidate agent modulates the activity of CCRL2.

A cell for use in a chemotactic assay may be any suitable cell expressing CCRL2. The cell may be transformed with a CCRL2 polynucleotide such that it expresses a CCRL2 polypeptide. Preferably the cell is a primary cell such as an endothelial cell which expresses the CCRL2 polypeptide. Suitable host cells include transient, or preferably stable higher eukaryotic cell lines, such as mammalian cells or insect cells, lower eukaryotic cells, such as yeast, or prokaryotic cells such as bacterial cells. Particular examples of cell lines include mammalian HEK293T, CHO, HeLa and COS cells. Preferably the cell line selected will be one which is not only stable, but also allows for mature glycosylation of a polypeptide. Chemotactic activity of a CCRL2 polypeptide may also be measured in transformed oocytes.

Methods of monitoring chemotactic activity are well documented in the art and kits are available. Suitable kits include, those using ChemoTx plates (Neuroprobe Inc.) or the BD Falcon HTS FluoroBlok 96-Multiwell Insert System (BD Biosciences Discovery Labware). Examples of chemotactic assays are described in the literature (for example, Biber et al., Journal of Leukocyte Biology 2003. 74:243-251; and Zuurman et al.; BCN annual report 1999-2001). The effect of a MIP-4 polypeptide acting on CCRL2 polypeptide can also be detected by changing the shape of the cells described in the literature (for example, Heineman et al., The Journal of Immunology 2003; 170:4752-4758; and Stubbs et al., Journal of Biological Chemistry 2002; 277:26012-26020).

The invention further provides an agent detected by any of the above-described methods and the use of such an agent in method of treatment of the human or animal body by therapy. The agent may be an agonist, partial agonist, antagonist or inverse agonist of CCRL2 activity. The invention further provides the use of an agent detected by any of the methods of the invention in the manufacture of a medicament for use in the treatment of an inflammatory disease or disorder, in the treatment of a disease or disorder associated with enhanced activation of macrophages or in the treatment of infection. A pharmaceutical composition comprising an agent of the invention and a pharmaceutically acceptable carrier or diluent is also provided.

A method of modulating the activity of a CCRL2 polypeptide in a cell is provided by the invention, which method comprises delivering an agent detected according to the invention the cell, such that the activity of CCRL2 is modulated. The cell may be in vivo or in vitro. The delivery of the agent is discussed in more detail below.

A method of treating an inflammatory disease or disorder, a method of treating a disease or disorder associated with enhanced macrophage activity and a method of treating an infection are also provided by the invention, which methods comprise administering a therapeutically effective amount of an agent according to the invention to an individual in need thereof.

A method of treating an inflammatory disease or disorder of the invention typically comprises:

(i) identifying an agent for the prevention or treatment of an inflammatory disease or disorder by a method according to the invention; and (ii) administering a therapeutically effective amount of an agent detected in (i) to an individual having an inflammatory disease or disorder.

Where CCRL2 activity or expression is reduced in a subject having an inflammatory disease or disorder, an agent for use in the treatment of the inflammatory disease or disorder is preferably an agonist or potentiator of CCRL2 activity or an agent which enhances expression of CCRL2. Where CCRL2 activity or expression is enhanced in a subject having an inflammatory disease or disorder, a therapeutic agent is typically an antagonist of CCRL2 activity or an inhibitor of expression. The agent may bind to a MIP-4 polypeptide that interacts with the CCRL2 receptor to prevent receptor activation, for example the agent may be an antibody to a MIP-4 polypeptide.

Where MIP-4 activity or expression is reduced in a subject having an inflammatory disease or disorder, an agent for use in the treatment of the inflammatory disease or disorder is preferably an agonist or potentiator of MIP-4 activity or an agent which enhances expression of MIP-4. Where MIP-4 activity or expression is enhanced in a subject having an inflammatory disease or disorder, a therapeutic agent is typically an antagonist of MIP-4 activity or an inhibitor of expression. The agent may bind to a CCRL2 polypeptide that interacts with MIP-4 and prevents receptor activation, for example the agent may be an antibody to a CCRL2 polypeptide.

In all the above embodiments, the inflammatory disease or disorder is preferably chronic obstructive pulmonary disease (COPD), bronchitis, emphysema, an inflammatory bone disorder, psoriasis, inflammatory bowel disease, an inflammatory brain disorder, atherosclerosis, endometriosis, autoimmune deficiency syndrome (AIDS), lupus erythematosus, allograft rejection, rheumatoid arthritis or allergic inflammation. The inflammatory brain disorder may be multiple sclerosis, or stroke or heamorrhage. The inflammatory bowel disease may be ulcerative colitis or Crohn's disease. The inflammatory bone disorder may be arthritis, including rheumatoid, autoimmune and infectious arthritis. The allergic inflammation may be, for example, asthma or contact dermatitis. The inflammatory disease or disorder may be a CCRL2-related or a MIP-4-related disease or disorder. An inflammatory disease or disorder may be present, or be suspected of being present, in the individual to be treated. The individual is discussed in more detail below.

A method of treating a disease or disorder associated with enhanced macrophage activity typically comprises:

(i) identifying an agent that modulates the activity of CCRL2 by a method according to the invention; and (ii) administering a therapeutically effective amount of an agent identified in (i) to an individual having the disease or disorder.

Increased levels of MIP-4 expression results in increased recruitment of macrophages expressing CCRL2. CCRL2 is also upregulated in activated macrophages. An agent for use in the treatment of a disease or disorder associated with enhanced macrophage activation is preferably an antagonist of MIP-4/CCRL2 activity or an agent which inhibits expression of MIP-4 or CCRL2. The agent may bind to a CCRL2 polypeptide that interacts with the MIP-4 and prevent receptor activation, for example the agent may be an antibody to a CCRL2 polypeptide. The agent may bind to a MIP-4 polypeptide that interacts with the CCRL2 receptor and prevent receptor activation, for example, the agent may be an antibody to a MIP-4 polypeptide.

The disease or disorder associated with enhanced macrophage activity may be one where increased levels of MIP-4 expression is found in the diseased tissue resulting in inappropriate recruitment of macrophages to the tissue. Such diseases or disorders include autoimmune disease and contact hypersensitivity, such as allergic dermatitis.

The disease or disorder associated with enhanced macophage activity may be one where abnormal macophage activity contributes to the disease or disorder or gives rise to symptoms or complications associated with the disease or disorder. CCRL2 is up-regulated in activated macophages and so inhibition of CCRL2 activation by MIP4 may prevent or ameliorate the symptoms of the disease or disorder. For example, macophages in fat significantly contribute to obesity and obesity related insulin resistance via chronic inflammation. Therefore, obesity and obesity-related insulin resistance are two examples of such disorders.

Increased levels of MIP-4 are associated with gastric cancer, childhood acute lymphoblastic leukaemia and ovarian carcinoma in all cases concomitant with the accumulation of macrophage like cells. Tissue-specific expression of particular chemokines also influences tumour growth and metastasis. Thus blocking the interaction between MIP-4 and CCRL2 may prevent the further infiltration of macrophage like cells and reduce tumour expansion. Cancer may thus be considered as a disease associated with enhanced macrophage activity. An agent of the invention which inhibits the interaction between MIP-4 and CCRL2 or which acts as a CCRL2 antagonist is useful in treating cancer, in particular gastric cancer, childhood acute lymphoblastic leukaemia and ovarian carcinoma.

Rheumatoid arthritis (RA) synovial fluid contains enhanced levels of many cytokines. The present inventor has shown for the first time that MIP-4 levels in RA synovial fluid significantly affect monocyte chemotaxis. The inventor has demonstrated that both MIP-4 induced chemotaxis and chemotaxis induced by RA synovial fluid can be blocked by a CCRL2 antibody and that removal of MIP-4 from RA synovial fluid reduces monocyte chemotaxis. Accordingly, inhibitors of CCRL2 activation by MIP-4 may be used in methods of treating rheumatoid arthritis. Suitable inhibitors include CCRL2 antagonists and partial agonists as well as anti-MIP-4 and anti-CCRL2 antibodies.

The individual having a disease or disorder associated with enhanced macrophage activity is discussed in more detail below.

A method of treating infection typically comprises:

(i) identifying an agent that modulates the activity of CCRL2 by a method according to the invention; and (ii) administering a therapeutically effective amount of an agent identified in (i) to an individual with the infection.

The agent identified in (i) is generally an agent which stimulates CCRL2 activity such that macrophages are recruited to the site of infection, i.e. the agent is preferably an agonist or potentiator of CCRL2 activity. The agent is preferably administered at the site of the infection. The agent may be administered systemically to stimulate macrophage activation more generally.

The infection may be an infection caused by any pathogenic organism, such as a virus, fungus or bacteria. Preferably the infection is a bacterial infection. The individual having an infection is discussed in more detail below.

Polypeptides and Polynucleotides Useful in the Invention

CCRL2 polypeptides useful in the invention include both the long form (CRAM-A) and short form (CRAM-B) of the receptor. Therefore CCRL2 polypeptides useful in the invention include those having the sequence of SEQ ID NO: 2 or 4. CCRL2 polypeptides useful in the invention also include variant polypeptides having amino acid sequences that are at least 80%, at least 90% or at least 95% identical to SEQ ID NO: 2 or 4 over its entire length that are functionally equivalent to CCRL2. Preferred variant polypeptides include CCRL2 homologues from other species such as monkey, dog, mouse, rat, guinea pig or zebra fish. Fragments of SEQ ID NO: 2 or 4 which are functionally equivalent to CCRL2 may also be used. Such fragments may be from 250 to 355 amino acids in length and are preferably at least 275, 300, 310, 320, 330 or 340 amino acids long. Functionally equivalent means that the CCRL2 polypeptide binds to a MIP-4 polypeptide and is capable of activating a CCRL2-linked signalling pathway. Generally binding of MIP-4 to the CCRL2 polypeptide stimulates a CCRL2 linked signalling pathway. Typically, the CCRL2 linked signalling pathway involves activation of Gi3. Typically, the CCRL2 polypeptide, "specifically binds" to a MIP-4 polypeptide. A CCRL2 polypeptide "specifically binds" to a MIP-4 polypeptide when it binds with preferential affinity to the MIP-4 polypeptide compared to other polypeptides. A variety of protocols for competitive binding are known in the art (discussed further below).

CCRL2 polynucleotides useful in the invention include polynucleotides that encode a CCRL2 polypeptide. CCRL2 polypeptides useful in the invention include polynucleotides that encode both the long form (CRAM-A) and short form (CRAM-B) of the receptor. The polynucleotide may comprise the sequence of SEQ ID NO: 1 or 3 or a sequence at least 90% or 95% identical to SEQ D NO: 1 or 3 over its entire length.

MIP-4 polypeptides useful in the invention include polypeptides having the sequence of SEQ ID NO: 6. MIP-4 polypeptides useful in the invention also include sequences at least 50%, 60%, 70%, 80%, 90% or 95% identical to SEQ ID NO: 6 over its entire length which binds to and activate a signalling activity of a CCRL2 polypeptide. MIP-4 polypeptides also include fragments of any of the above-mentioned MIP-4 polypeptides which bind to and activate a signalling activity of a CCRL2 polypeptide. Fragments preferably retain at least 50%, at least 60%, at least 70%, at least 80% or at least 90% of the binding activity and level of signalling activation of SEQ ID NO: 8. MIP-4 polypeptides can comprise additions, insertions, deletions or substitutions of SEQ ID NO: 6 as long as the resulting polypeptide specifically binds to and activates a signalling activity of a CCRL2 polypeptide and preferably retains at least 50%, at least 60%, at least 70%, at least 80% or at least 90% of the binding activity and level of signalling activation of SEQ ID NO: 6.

Typically, the MIP-4 polypeptide "specifically binds" to a CCRL2 polypeptide. A MIP-4 polypeptide "specifically binds" to a CCRL2 polypeptide when it binds with preferential affinity to the CCRL2 polypeptide compared with other receptor polypeptides. A variety of protocols form competitive binding are known in the art.

Polynucleotides that encode a MIP-4 polypeptide are also useful in the invention. Polynucleotides useful in the invention include polynucleotides that encode a MIP-4 polypeptide. The polynucleotide may comprise the sequence of SEQ ID NO: 5 or a sequence at least 50%, 60%, 70%, 80%, 90% or 95% identical to SEQ ID NO: 5 over its entire length.

The above mentioned identity may be calculated on the basis of nucleotide or amino acid identity (sometimes referred to as "hard homology").

For example the UWGCG Package provides the BESTFIT program which can be used to calculate homology (for example used on its default settings) (Devereux et al. (1984) *Nucleic Acids Research* 12, p387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al. (1990) J Mol Biol 215:403-10.

A BLAST analysis is preferably used for calculating identity. Software for performing BLAST analyses is publicly available through the National Center for Biotechnology Information (http://www.ncbi.nln.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequences typically differ by at least 1, 2, 5, 10, 20 or more mutations (which may be substitutions, deletions or insertions of nucleotide or amino acids). These mutations may be measured across any of the regions mentioned above in relation to calculating identity. In the case of proteins the substitutions are preferably conservative substitutions. These are defined according to the following Table. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Any of the polypeptides useful in the invention may be in the form of a dimer. Any of the polypeptides useful in the invention may further be chemically-modified to form a derivative. Derivatives include polypeptides that have lipid extensions or have been glycosylated. Derivatives also include polypeptides that have been detectably labelled. Detectably labelled polypeptides have been labelled with a labelling moiety that can be readily detected. Examples of labelling moieties include, but are not limited to, radioisotopes or radionucleodtides, fluorophores such as green fluorescent protein (GFP), electron-dense reagents, quenchers of fluorescence, enzymes, affinity tags and epitope tags. Preferred radioisotopes include tritium and iodine. Affinity tags are labels that confer the ability to specifically bind a reagant onto the labelled molecule. Examples include, but are not limited to, biotin, histidine tags and glutathione-S-transferase (GST). Labels may be detected by, for example, spectroscopic, photochemical, radiochemical, biochemical, immunochemical or chemical methods that are known in the art.

Any of the polypeptides useful in the invention may also comprise additional amino acids or polypeptide sequences. A preferred polypeptide useful in the invention is a MIP-4 polypeptide with an additional methionine residue attached to the amino terminus (Met-MIP-4) or the carboxy terminus. Any of the polypeptides useful in the invention may comprise additional polypeptide sequences such that they form fusion proteins. The additional polypeptide sequences may be fused at the amino terminus, carboxy terminus or both the amino terminus and the carboxy terminus of MIP-4. Examples of fusion partners include, but are not limited to, GST, maltose binding protein, alkaline phosphatates, thiorexidin, GFP, histidine tags and epitope tags (for example, Myc or FLAG). CCRL2 polypeptides may be fused to a GTP-binding protein (G protein).

Antibodies Useful in the Invention

The invention also provides the use of an antibody specific for a MIP-4 polypeptide for the treatment of a CCRL2-related disease or disorder. The invention also provides the use of an antibody specific for a CCRL2 polypeptide for the treatment of a MIP-4-related disease or disorder.

Antibodies may be raised which bind to a MIP-4 polypeptide or a CCRL2 polypeptide. Antibodies may be raised which bind to both a MIP-4 polypeptide and a CCRL2 polypeptide. Antibodies may be raised against MIP-4 fusion proteins such as Met-MIP-4. Typically, the antibody "specifically binds" or "is specific for" a MIP-4 polypeptide or a CCRL2 polypeptide. The antibody may bind to a glycosylation site on CCRL2. An antibody, or other compound, "specifically binds" to a polypeptide or is "specific for" a polypeptide when it binds with preferential affinity to the protein for which it is specific compared to other polypeptides, such as chemokine or G-protein receptor. A variety of protocols for competitive binding or immunoradiometric assays to determine the specific binding capability of an antibody are well known in the art (see for example Maddox et al., J. Exp. Med. 158, 1211-1226, 1993). Such immunoassays typically involve the formation of complexes between the specific protein and its antibody and the measurement of complex formation.

For the purposes of this invention, the term "antibody", unless specified to the contrary, includes fragments which bind a polypeptide. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies.

Antibodies can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising an antibody in a host animal against the whole polypeptide or a fragment thereof, for example an antigenic epitope thereof, herein after the "immunogen". The fragment may be any of the fragments mentioned herein (typically at least 10 or at least 15 amino acids long) and comprise a polymorphism (such as any of the polymorphisms mentioned herein).

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified.

A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat, mouse, guinea pig, chicken, sheep or horse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Antibodies that bind to MIP-4 are known in the art and commercially available (for example, from Novus Biologicals® and R&D Systems).

Uses of MIP-4 Polypeptides, Polynucleotides and Antibodies

The invention provides a method of activating a CCRL2 signalling pathway in a cell, which method comprises introducing a MIP-4 polypeptide to a cell. The cell may be in vivo or in vitro. The delivery of the agent is discussed in more detail below.

The invention further provides the use of:
(i) a MIP-4 polypeptide;
(ii) a polynucleotide that encodes a MIP-4 polypeptide; or
(iii) an antibody specific for a MIP-4 polypeptide;

in the manufacture of a medicament for the treatment of a CCRL2-related disease or disorder. The CCRL2-related disease or disorder is preferably a CCRL2 mediated inflammatory disease such as inflammatory bowel disease, endometriosis, atherosclerosis or an inflammatory brain disorder. The inflammatory brain disorder may be multiple sclerosis, or stroke or heamorrhage. The inflammatory bowel disease may be ulcerative colitis or Crohn's disease. A CCRL2-related disease or disorder may be present, or be suspected of being present, in the individual to be treated. The individual may have a genetic predisposition to a CCRL2-related disease or disorder, such as a polymorphism.

The individual is discussed in more detail below.

Uses of CCRL2 Polypeptides, Polynucleotides and Antibodies

The invention provides the use of:
(i) a CCRL2 polypeptide;
(ii) a polynucleotide that encodes a CCRL2 polypeptide; or
(iii) an antibody specific for a CCRL2 polypeptide;

in the manufacture of a medicament for the treatment of a MIP-4-related disease or disorder. The MIP-4-related disease or disorder is preferably allergic inflammation, such as asthma or contact dermatitis. The MIP-4 related disease may be cancer as increased levels of MIP-4 are associated with gastric cancer, childhood acute lymphoblastic leukaemia and ovarian carcinoma.

A MIP-4-related disease or disorder may be present, or be suspected of being present, in the individual to be treated. The individual may have a genetic predisposition to a MIP-4-related disease or disorder, such as a polymorphism. The individual is discussed in more detail below.

Methods of Diagnosis

The invention further provides methods of diagnosing a CCRL2-related disease or disorder or an MIP-4-related disease or disorder in an individual. A CCRL2-related disease or disorder is typically a disease or disorder which is associated with the CCRL2 gene. For example, a polymorphism in the CCRL2 gene region may be associated with the disease or disorder. A MIP-4-related disease or disorder is one which is associated with the MIP-4 gene. For example, a polymorphism in the MIP-4 gene region may be associated with the disease or disorder.

The CCRL2-related disease or disorder is preferably a CCRL2-mediated inflammatory disease such as inflammatory bowel disease endometriosis, atherosclerosis or an inflammatory brain disorder. The inflammatory brain disorder may be multiple sclerosis, or stroke or heamorrhage. The inflammatory bowel disease may be ulcerative colitis or Crohn's disease. A CCRL2-related disease or disorder may be present, or be suspected of being present, in the individual to be diagnosed. The MIP-4-related disease or disorder is preferably allergic inflammation, such as asthma or contact dermatitis. A MIP-4-related disease or disorder may be present, or be suspected of being present, in the individual to be treated. The individual is discussed in more detail below.

In a first diagnostic embodiment of the invention, the method of diagnosis comprises carrying out an amplification reaction on a sample isolated from an individual using primers specific for MIP-4. The presence or absence of a polynucleotide encoding a MIP-4 polypeptide in the sample is then determined. The absence of a polynucleotide encoding a MIP-4 polypeptide is indicative of the presence of a CCRL2-related disease or disorder. If the polynucleotide is present, the amount of the amplified polynucleotide is compared with a standard and a difference in the amount relative to the standard is indicative of the presence of a CCRL2-related disease or disorder in the individual. The standard refers to the equivalent measurement in an individual not affected by the CCRL2-related disease or disorder.

The methods of the first diagnostic embodiment also comprise carrying out an amplification reaction on a sample isolated from an individual using primers specific for CCRL2. The presence or absence of a polynucleotide encoding a CCRL2 polypeptide in the sample is then determined. The absence of a polynucleotide encoding a CCRL2 polypeptide is indicative of the presence of a MIP-4-related disease or disorder. If the polynucleotide is present, the amount of the amplified polynucleotide is compared with a standard and a difference in the amount relative to the standard is indicative of the presence of a MIP-4-related disease or disorder in the individual. The standard refers to the equivalent measurement in an individual not affected by the MIP-4-related disease or disorder.

The amount of polynucleotide maybe measured by any suitable method such as quantitative or semi-quantitative polymerase chain reaction (PCR). In these methods, part of polynucleotide in the sample is copied (or amplified) prior to determining the amount. Methods of "quantitative" amplification are well known in the art (PCR Protocols, A Guide to Methods and Applications, Innis et al., Academic Press, Inc. N.Y., (1990)).

Figure 4:
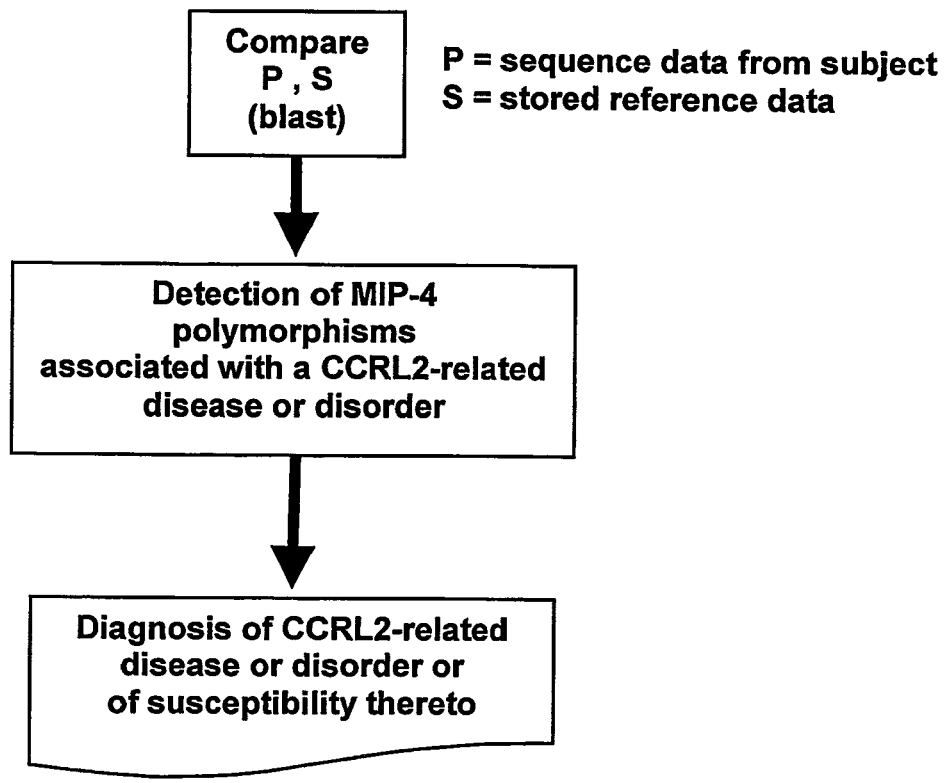
FIG. 4 is a flow diagram setting out the steps of a computed-implemented method of diagnosing a CCRL2-related disease or disorder in an individual.

In a second diagnostic embodiment, the method of diagnosis comprises amplifying a polynucleotide encoding MIP-4 from a sample isolated from an individual. The presence of a mutation or polymorphism associated with associated with a CCRL2-related disease or disorder is then determined. In one embodiment, the sequence of an amplified polynucleotide is compared with sequence information relating to sequences associated with CCRL2-related diseases or disorders (FIG. 4). Such information typically indicates sequence polymorphisms associated with said diseases or disorders.

Figure 5:
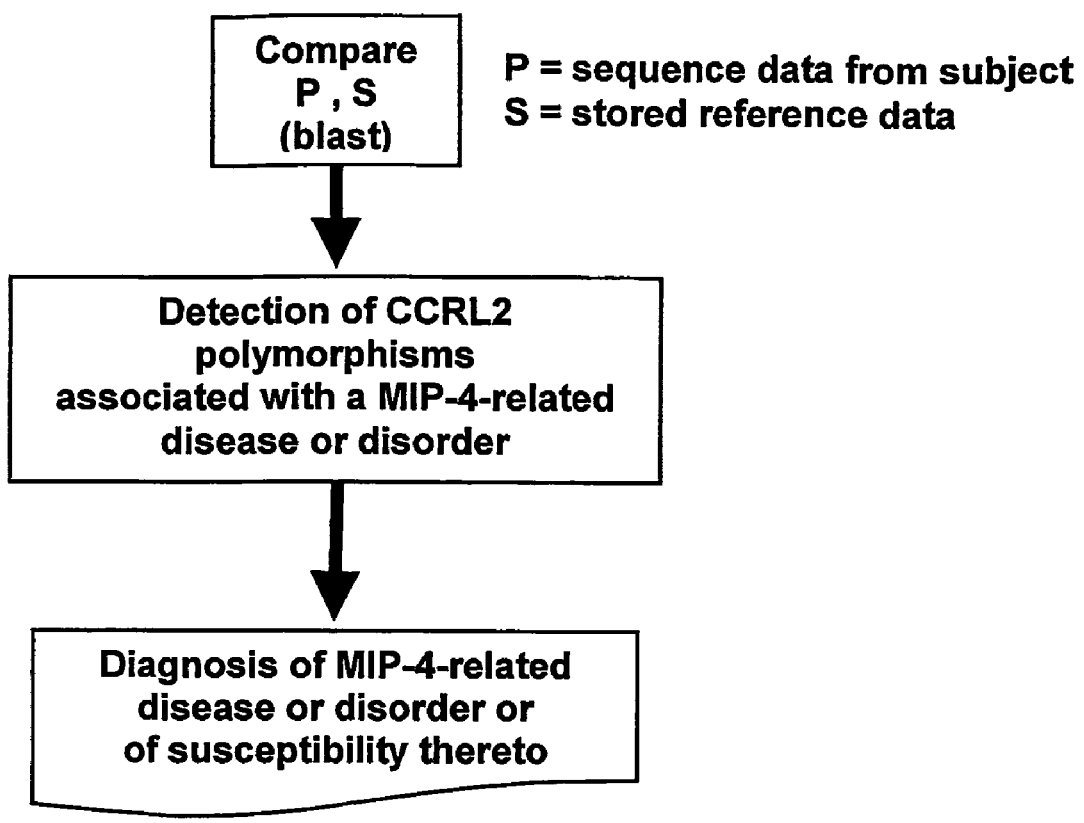
FIG. 5 is a flow diagram setting out the steps of a computed-implemented method of diagnosing a MIP-4-related disease or disorder in an individual.

The methods of the second diagnostic embodiment also comprise amplifying a polynucleotide encoding CCRL2 from a sample isolated from an individual. The presence of a mutation or polymorphism associated with associated with a MEP-4-related disease or disorder is then determined. In one embodiment, the sequence of an amplified polynucleotide is compared with sequence information relating to sequences associated with MIP-4-related diseases or disorders (FIG. 5). Such information typically indicates sequence polymorphisms associated with said diseases or disorders.

The mutation or polymorphism is typically detected by directly determining the presence of the mutation or polymorphism sequence in a polynucleotide of the individual. Such a polynucleotide is typically genomic DNA, mRNA or cDNA. The polymorphism may be detected by any suitable method such as those mentioned below.

The diagnostic method may comprise detecting the presence or absence of a mutation or polymorphism using a specific binding agent. A specific binding agent is an agent that binds with preferential or high affinity to the protein or polynucleotide having the polymorphism but does not bind or binds with only low affinity to other polypeptides or proteins (such as a MIP-4 polynucleotide or CCRL2 polynucleotide which does not comprise the mutation or polymorphism).

The specific binding agent may be a probe or primer. The probe may be a protein (such as an antibody) or an oligonucleotide. The probes or primers will typically also bind to flanking nucleotides and amino acids on one or both sides of the polymorphism, for example at least 2, 5, 10, 15 or more flanking nucleotide or amino acids in total or on each side. Thus a probe or primer may be fully or partially complementary to either all or part of the flanking 5' and/or 3' sequences of the mutation or polymorphism. The probe may be labelled or may be capable of being labelled indirectly. The binding of the probe to the polynucleotide or protein may be used to immobilise either the probe or the polynucleotide or protein.

Generally, determination of the specific binding of the agent to the mutation or polymorphism can be done by determining the binding of the agent to the polynucleotide of the individual. However, the agent may also be able to bind the corresponding wild-type sequence, for example by binding the nucleotides which flank the mutation or polymorphism position. In such a case, the manner of binding to the wild-type sequence will be detectably different to the binding of a polynucleotide or protein containing the polymorphism.

Oligonucleotide ligation assays involve the use of two oligonucleotide probes. These probes bind to adjacent areas on the polynucleotide which contains the mutation or polymorphism, allowing (after binding) the two probes to be ligated together by an appropriate ligase enzyme. However the presence of single mismatch within one of the probes may disrupt binding and ligation. Thus ligated probes will only occur with a polynucleotide that contains the mutation or polymorphism, and therefore the detection of the ligated product may be used to determine the presence of the mutation or polymorphism.

Probes may also be used in a heteroduplex analysis based system. In such a system when the probe is bound to polynucleotide sequence containing the mutation or polymorphism it forms a heteroduplex at the site where the polymorphism occurs (i.e. it does not form a double strand structure). Such a heteroduplex structure can be detected by the use of single or double strand specific enzyme. Typically the probe is an RNA probe, the heteroduplex region is cleaved using RNAase H and the polymorphism is detected by detecting the cleavage products.

Mutations or polymorphisms may also be detected using fluorescent chemical cleavage mismatch analysis which is described for example in PCR Methods and Applications 3, 268-71 (1994) and Proc. Natl. Acad. Sci. 85, 4397-4401 (1998).

Alternatively, a PCR primer is used that primes a PCR reaction only if it binds a polynucleotide containing the mutation or polymorphism (i.e. a sequence- or allele-specific PCR system) and the presence of the mutation or polymorphism may be determined by the detecting the PCR product. Preferably the region of the primer which is complementary to the mutation or polymorphism is at or near the 3' end of the primer. The presence of the polymorphism may be determined using a fluorescent dye and quenching agent-based PCR assay such as the Taqman PCR detection system.

A specific binding agent may be capable of specifically binding the amino acid sequence encoded by a mutated or polymorphic sequence. For example, the agent may be an antibody or antibody fragment. The detection method may be based on an ELISA system.

The method may be an RFLP based system. This can be used if the presence of the polymorphism in the polynucleotide creates or destroys a restriction site that is recognised by a restriction enzyme.

The presence of the mutation or polymorphism may be determined based on the change which the presence of the mutation or polymorphism makes to the mobility of the polynucleotide during gel electrophoresis. In the case of a polynucleotide single-stranded conformation polymorphism (SSCP) or denaturing gradient gel electrophoresis (DDGE) analysis may be used.

In another method of detecting the mutation or polymorphism, a polynucleotide comprising the polymorphic region is sequenced across the region which contains the polymorphism to determine the presence of the polymorphism. The methods of the second diagnostic embodiment may be carried out using an array, such as a DNA chip. For example, a probe may be immobilised on a DNA chip.

In a third diagnostic embodiment the invention, the method of diagnosis comprises contacting a sample isolated from an individual which comprises a CCRL2 peptide with a MIP-4 polypeptide under conditions which permit the binding of the MIP-4 polypeptide to the CCRL2 polypeptide. The activity of the CCRL2 polypeptide is then measured. The activity of this CCRL2 polypeptide is then compared with a standard and a difference in the activity relative to the standard indicative of the presence of a CCRL2-related disease or disorder in the individual. This standard refers to the equivalent measurement in an individual not affected by the CCRL2-relevant disease or disorder.

The methods of the third diagnostic embodiment also comprise contacting a sample isolated from an individual which comprises a MIP-4 polypeptide with a CCRL2 polypeptide under conditions which permit the binding of the MIP-4 polypeptide to the CCRL2 polypeptide. The activity of the CCRL2 polypeptide is then measured. The activity of this CCRL2 polypeptide is then compared with a standard and a difference in the activity relative to the standard indicative of the presence of a MIP-4-related disease or disorder in the individual. This standard refers to the equivalent measurement in an individual not affected by the MIP-4-relevant disease or disorder.

The conditions which permit the binding of a MIP-4 polypeptide to a CCRL2 polypeptide are, for example, the temperature, salt concentration, pH and protein concentration under which a MIP-4 polypeptide binds to a CCRL2 polypeptide. Exact binding conditions will vary depending on nature of the assay, for example, when the assay uses viable cells or only membrane fraction of cells. However, because CCLR2 is a cell surface receptor and MIP-4 polypeptides are secreted polypeptides that interact with the extracellular domain of CCRL2, preferred conditions will generally include physiological salt concentration (approx 90 mM) pH about (7.0 to 8.0). Temperatures for binding may vary from 4° C. through to 37° C., but is preferably 4° C. The concentration of the MIP-4 polypeptide will also vary, but will preferably be from about 0.1 pM to about 10 µM.

The methods of all the diagnostic embodiments are carried out in vitro on a sample from the individual. The sample typically comprises a body fluid and/or cells of the individual and may, for example, be obtained using a needle and syringe or using a swab, such as a mouth swab. The sample may be a blood, urine, saliva, skin, cheek cell or hair root sample. The sample is preferably a blood sample comprising monocytes. The sample is typically processed before the method is carried out, for example DNA extraction may be carried out, the cells may be cultured or a membrane faction may be prepared from the cells. The polynucleotide or protein in the sample may be cleaved either physically or chemically (e.g. using a suitable enzyme). In one embodiment the part of polynucleotide in the sample is copied (or amplified), e.g. by cloning or using a PCR based method prior to determining the presence of mutations or polymorphisms.

Bioinformatics

The invention provides a method for determining the presence of a MIP-4 mutation or polymorphism associated with a CCRL2-related disease or disorder or a CCRL2 mutation or polymorphium associated with a MIP-4-related disease or disorder. The sequence of a MIP-4 polynucleotide or polypeptide associated with a CCRL2-related disease or disorder may be stored in an electronic format, for example in a computer database. The sequence of a CCRL2 polynucleotide or polypeptide associated with a MIP-4-related disease or disorder may be stored in an electronic format, for example in a computer database. The database may include further information about the polynucleotides or polypeptides. For example, the database may provide one or more aspects of the following types of information: the level of association of the polynucleotide or polypeptide with a disease or disorder, the frequency of the polynucleotide or polypeptide in patients suffering from the disorder, the probability of a patient having that polynucleotide or polypeptide developing a disease or disorder, the interaction of the polynucleotide or polypeptide with a therapeutic agent.

Diagnostic methods of the invention may be carried out by electronic means, for example using a computer system. Accordingly, the present invention provides a method for diagnosing a CCRL2-related disease or disorder or determining susceptibility of an individual to a CCRL2-related disease or disorder, which method comprises determining whether individual has a MIP-4 polynucleotide or polypeptide comprising a mutation associated with by a CCRL2-related disease or disorder by:

(i) optionally obtaining MIP-4 sequence data from a sample taken from an individual;

(ii) inputting MIP-4 sequence data from said individual to a computer;

(iii) comparing said data to stored MIP-4 sequence data stored in a computer database, which database comprises information relating MIP-4 sequence data to a CCRL2-related disease or disorder; and (iv) determining on the basis of said comparison the presence or absence of a CCRL2-related disease or disorder in said individual or whether said individual is susceptible to a CCRL2-related disease or disorder.

Accordingly, the present invention also provides a method for diagnosing a MIP-4-related disease or disorder or determining susceptibility of an individual to a MIP-4-related disease or disorder, which method comprises determining whether the individual has a polynucleotide or polypeptide comprising a mutation associated with a MIP-4-related disease or disorder with by:

(i) optionally obtaining CCRL2 sequence data from a sample taken from an individual;

(ii) inputting CCRL2 sequence data from said individual to a computer;

(iii) comparing said data to stored CCRL2 sequence data stored in a computer database, which database comprises information relating CCRL2 sequence data to a MIP-4-related disease or disorder; and (iv) determining on the basis of said comparison the presence or absence of a MIP-4-related disease or disorder in said individual or whether said individual is susceptible to a MIP-4 related disease or disorder.

MIP-4 or CCRL2 sequence data may be obtained from said sample by any suitable means such as those discussed herein. The sequence of all or part of the MIP-4 or CCRL2 gene may be obtained. Standard sequencing protocols known in the art may be used to obtain sequence data.

The MIP-4 sequence data or the CCRL2 sequence data may be stored in a database comprising information relating to two or more mutations or polymorphisms which are associated with a CCRL2-related disease or disorder or a MIP-4-related disease or disorder, including polymorphisms in the MIP-4 and/or CCRL2 genes and mutations or polymorphisms in genes other than the MIP-4 or CCRL2 genes.

The invention also provides apparatus comprising means for determining the susceptibility of an individual to a CCRL2-related disease or disorder, or a MIP-4-related disease or disorder, based on the presence of mutations or polymorphisms present in the MIP-4 gene and/or CCRL2 gene of said individual.

The invention further provides a computer program comprising program code means that, when executed on a computer system, instruct the computer system to perform a method of diagnosis according to the invention. Also provided is a computer program product comprising either a computer-readable storage medium having recorded thereon a computer program or program code means on a carrier wave that, when executed on a computer system, instruct the computer system to perform a method of the invention.

Individual

In all the therapeutic and diagnostic embodiments discussed above, the individual is typically a mammalian individual, for example a mammal kept as a pet or for agricultural or sporting reasons. In one embodiment the mammal is one in which CCRL2-related disease or disorder occurs naturally (without intervention by man). The mammal may be a bovine, porcine, canine, feline, rodent (such as a mouse, rat or hamster) or primate animal. In a preferred embodiment the individual is a human individual.

Kits

The invention provides various kits for detecting agents that modulate the activity of CCRL2. These kits comprise:
  (i) a MIP-4 polypeptide and (ii) a CCRL2 polypeptide or an isolated polynucleotide encoding a CCRL2 polypeptide;
  a MIP-4 polypeptide and a cell transformed with a polynucleotide encoding a CCRL2 polypeptide; or
  a MIP-4 polypeptide and a cell membrane fraction comprising a CCRL2 polypeptide.

The kit may additionally comprise one or more other reagents or instruments which enable any of the embodiments of the methods mentioned above to be carried out. Such reagents or instruments include one or more of the following: a means to detect the binding of the agent to the CCRL2-polypeptide, a detectable label (such as a fluorescent label), an enzyme able to act on a polynucleotide (typically a polymerase, restriction enzyme, ligase, RNAse H or an enzyme which can attach a label to a polynucleotide), suitable buffer(s) (aqueous solutions) for enzyme reagents, PCR primers, a positive and/or negative control, a gel electrophoresis apparatus, a means to isolate DNA from sample, a means to obtain a sample from the individual (such as an instrument comprising a needle) or a support comprising wells on which detection reactions can be done.

Yeast Cells

The invention further provides the use in a method of the invention of yeast cells transformed (or transfected) with a CCRL2 polynucleotide. Methods for the transformation (or transfection) of yeast cells are well known in the art (Davey et al., Pheromone procedures in Fission yeast, 1995, In: Microbial Gene Techniques: Methods in Molecular Genetics 6B. Adolph, K. W. San Diego: Academic Press: 247-263 and Ladds et al., Molecular Microbiology, 2003; 47(3), 781-792).

The CCRL2 polynucleotide preferably comprises the sequence of SEQ ID NO: 1 or 3 or a sequence at least 90% or 95% identical to SEQ ID NO: 1 or 3 over its entire length. CCRL2 polynucleotides can be introduced to cells using lithium acetate, electroporation or spheroplast transformation (Davey et al., Pheromone procedures in Fission yeast, 1995, In: Microbial Gene Techniques: Methods in Molecular Genetics 6B. Adolph, K. W. San Diego: Academic Press: 247-263 and Ladds et al., Molecular Microbiology, 2003; 47(3), 781-792). CCRL2 polynucleotides may also be incorporated into a recombinant vector. Preferably, a CCRL2 polynucleotide in a vector is operably linked to a control sequence which is capable of providing for the expression of the coding sequence by the host yeast cell, i.e. the vector is an expression vector. Such expression vectors can be used to express the CCRL2 polypeptide.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different CCRL2 polynucleotide may be introduced into the vector.

Such vectors may be transformed into a suitable host yeast cell to provide for expression of a CCRL2 polypeptide. Thus, a CCRL2 polypeptide can be obtained by cultivating a host yeast cell transformed or transfected with an expression vector as described above under conditions to provide for expression of the polypeptide, and recovering the expressed polypeptide. More preferably, such host cells may be used in the screening methods of the invention.

Any suitable vector may be used to express a CCRL2 polypeptide in the yeast cell. The vectors may be for example a plasmid vector provided with an origin of replication, optionally a promoter for the expression of the said polynucleotide and optionally a regulator of the promoter. The vectors may contain one or more selectable marker genes, for example URA3, HIS3, LEU2, TRP1, LYS2 or a tetracycline resistance gene. Promoters and other expression regulation signals may be selected to be compatible with the host cell for which the expression vector is designed. Multiple copies of the same or different CCRL2 polynucleotide in a single expression vector, or more than one expression vector each including a CCRL2 polynucleotide which may be the same or different may be transformed into the host cell.

The promoter sequence is preferably a promoter sequence derived from a yeast cell and in particular *Saccharomyces cerevisiae* or *Schizosaccharomyces pombe*. Suitable promoters for the expression of the CCRL2 polynucleotide in yeast cells include GAL, GAL10, PHO5, ADHI, PGK and GPD I (Schneider and Guarente, Methods Enzymol., 1991; 194: 373-388) and the thiamine repressible nmt-1 promoter (Ladds et al., Molecular Microbiology, 2003; 47(3), 781-792). Suitable expression vectors for the expression of the CCRL2 polynucleotide in yeast cells include pBM150, pYEp51, pLGSD5, YEp51, pAM82, pYE4, pAAh5, pMA56, pAH9/10/21, pMA230, pMA91 and pG-1/2 (Schneider and Guarente, Methods Enzymol., 1991; 194: 373-388. The promoter or vector will be chosen to be compatible with the host yeast cell that is to be transformed.

Preferably, the yeast is *Saccharomyces cerevisiae* or *Schizosaccharomyces pombe*.

In one embodiment, the yeast cells may be G protein transplants in which at least 5, at least 10, at least 15 or at least 20 amino acids at the carboxy terminal of the yeast Gα subunit have been replaced with the corresponding residues from a non-yeast, preferably human, G protein. Preferably, the C terminal 5 amino acids are replaced with the corresponding residues of a human G protein. Preferably, the human G protein corresponds to the G protein which the CCRL2 polypeptide naturally interacts with so that the expression of the CCRL2 polypeptide in the yeast cell results in a functional association with the transplanted G protein. The functional association enables the CCRL2 polypeptide to activate the yeast cell signalling machinery. A reporter gene under the control of a promoter which is activated by the yeast cell machinery may be introduced into the yeast cell. Reporter gene expression may then be used to monitor CCRL2 activity. Suitable reporter genes include LacZ and GFP. The reporter gene may be integrated into the yeast cell chromosome. The yeast cell may be derived from a sxa2>lacZ reporter strain (Didmon et al., Curr. Genet., 2002; 41: 241-253 and Ladds et al., Molecular Microbiology, 2003; 47(3), 781-792).

The G-protein transplant yeast cells of the invention may be used in the screening methods of the invention. Suitable non-yeast G proteins include Gpa1, Gs, Gi, Go, Gq, Gz, G12, G13, G14 and G16. The G protein is preferably Gi and more preferably Gi3.

The G protein transplant cells may be generated as described in Ladds et al., Molecular Microbiology, 2003; 47(3), 781-792.

Accordingly, a preferred yeast cell provided by the invention comprises a CCRL2 polypeptide, a Gi3 protein and, optionally, a reporter construct. The CCRL2 polypeptide preferably comprises the sequence show in SEQ ID NO: 2 or 4. The Gi3 protein preferably comprises 5 carboxy terminal residues from human Gi3 fused to a yeast G protein in which the corresponding 5 carboxy terminal residues have been deleted.

Administration or Delivery

When administration is for the purpose of treatment, administration may be either for prophylactic or therapeutic purpose. When provided prophylactically, the agent or polypeptide, polynucleotide or antibody is provided in advance of any symptom. The individual may have been identified as having a genetic predisposition to an inflammatory disease or disorder. For example, where the inflammatory disease or disorder is a CCRL2-related disease or disorder, such as inflammatory bowel disease, atherosclerosis, endometriosis or an inflammatory brain disease the individual may have a polymorphism in the CCRL2 gene which polymorphism is associated with the disease or disorder. The prophylactic administration of the agent or polypeptide, polynucleotide or antibody serves to prevent or attenuate any subsequent symptom. When provided therapeutically the agent or polypeptide, polynucleotide or antibody is provided at or following, preferably shortly after, the onset of a symptom. The therapeutic administration of the agent or polypeptide, polynucleotide or antibody serves to attenuate any actual symptom. Administration and therefore the methods of the invention may be carried out in vivo or in vitro.

The formulation of any of the therapeutic agents mentioned herein, including polypeptides, polynucleotides and antibodies, will depend upon factors such as the nature of the agent and the condition to be treated. Any such agent may be administered or delivered in a variety of dosage forms. It may be administered or delivered orally (e.g. as tablets, troches, lozenges, aqueous or oily suspensions, dispersible powders or granules), parenterally, subcutaneously, intravenously, intramuscularly, intrasternally, transdermally or by infusion or inhalation techniques. The agent may also be administered or delivered as suppositories. A physician will be able to determine the required route of administration or delivery for each particular patient.

Typically the agent is formulated for use with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuff; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

A therapeutically effective amount of agent is administered. A therapeutically effective amount of an agent is an amount that alleviates the symptoms or which prevents or delays the onset of symptoms of an inflammatory disease or disorder.

The dose may be determined according to various parameters, especially according to the substance used; the age, weight and condition of the patient to be treated; the route of administration; and the required regimen. Again, a physician will be able to determine the required route of administration and dosage for any particular patient. A typical daily dose is from about 0.1 to 50 mg per kg, preferably from about 0.1 mg/kg to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The present invention is described with reference to the following, non-limiting Examples:

EXAMPLE 1

CCRL2 Signalling Assays

Yeast Strains

Yeast strains were constructed as described in Ladds et al., Molecular Microbiology, 2003; 47(3), 781-792.

Yeast Assays

All assays were performed by Septegen's standard protocols (Ladds et al., Molecular Microbiology, 2003; 47(3), 781-792). Yeast strains were incubated with ligand for 16 hours prior to assaying LacZ activity.

CCRL2 Activity in the Presence of MIP-4

MIP-4 was received from R&D Systems and stored at −20° C. until use. MIP-4 was dissolved in growth medium containing 0.1% BSA to provide a stock solution of 11.1 µM (50 µg of chemokine in final volume of 577 µl). For the initial screen of the G-protein transplant strains, 210 µl of the 11.1 µM stock was diluted to a final volume of 2.1 ml to give a working concentration of 1.11 µM.

For each of the G-transplant strains, 180 µl of 1.11 µM solution was added to 20 µl of cells. The final assay volume was 200 µl and the final concentration of MIP-4 was 1 µM. MIP-4 activated the short form of CCRL2 (CRAM-B) in Gi3 transplant strains (FIG. 1).

Figure 2:
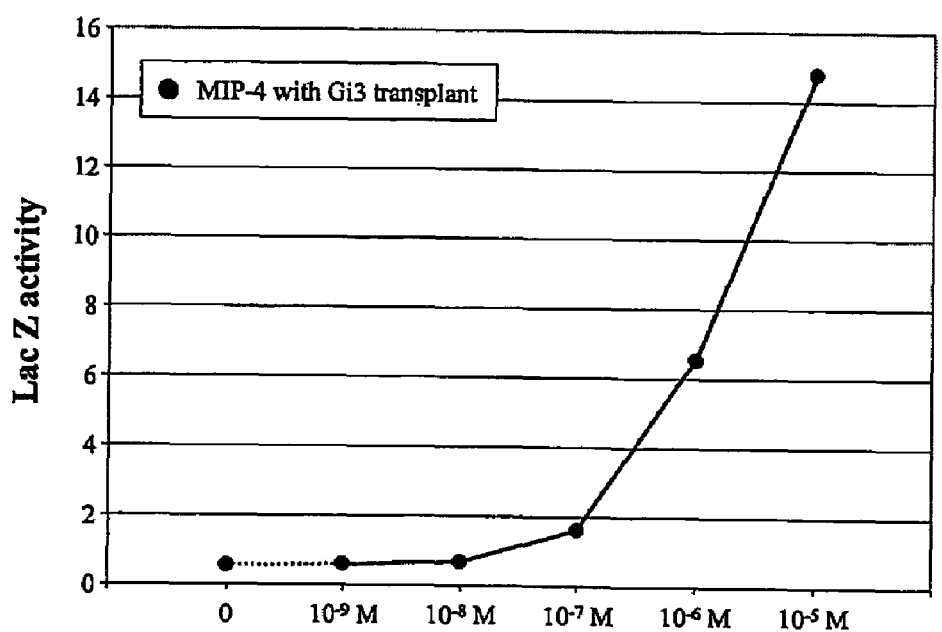
FIG. 2 shows the LacZ activity in Gi3 transplant yeast cells at varying concentrations of MIP-4. LacZ activity is expressed per $10^6$ cells.

On the basis of the initial screen against all of the G-transplants, MIP-4 was assayed against the Gi3-transplant at a range of concentrations. A series of 10-fold dilutions were made from the 11.1 µM stock (30 µl plus 270 µl). For each sample, 180 µl of the appropriately diluted stock was added to 20 µl of cells (final concentrations of 10 µM, 1 µM etc.). The response of the Gi3 transplant cells increased exponentially with increasing concentrations of MIP-4 (FIG. 2).

Control Experiments

Figure 3:
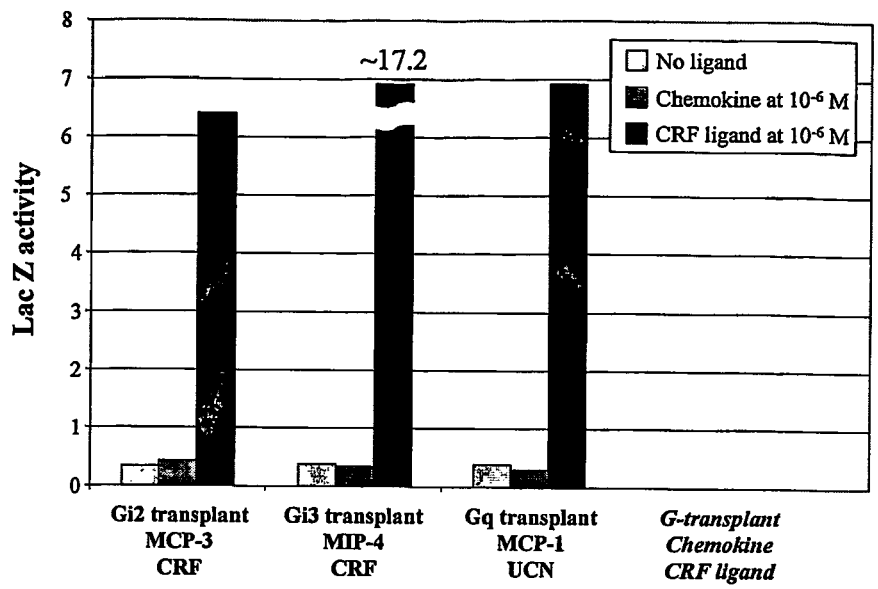
FIG. 3 shows the LacZ activity in the G-protein transplant yeast cells expressing the Corticotrophin Releasing Factor Receptor (CRFR). LacZ activity is expressed per $10^6$ cells.

To confirm that the responses reported for the various chemokines are dependent upon the CCRL2 receptor, all three chemokines were assayed against appropriate yeast strains expressing the Corticotropin Releasing Factor Receptor (CRFR). This was chosen as control strain since it has peptide agonists and interacts with the Gq, Gi2 and Gi3 transplants and the interaction is dependent upon the identity of the ligand. MIP-4 was active against the short form of CCRL2 (CRAM-B) in the Gi3-transplant ($10^{-6}$ M resulted in ~6.5 LacZ units) (FIG. 3). Monocyte chemotactic protein-1 (MCP-1) was active against the short form of CCRL2 (CRAM-B) in the Gq-transplant ($10^{-6}$ M resulted in ~5.7 LacZ units) (FIG. 3). Monocyte chemotactic protein-3 (MCP-3) was active against the short form of CCRL2 (CRAM-B) in the Gi2-transplant ($10^{-6}$ M resulted in ~2.2 LacZ units) (FIG. 3).

Corticotrophin releasing factor (CRF) was active against CRF-R1 in the Gi2-transplant ($10^{-6}$ M resulted in ~6.4 LacZ units) and the Gi3-transplant ($10^{-6}$ M resulted in ~17.2 LacZ units) (FIG. 3). Urocortin was active against CRF-R1 in the Gq-transplant ($10^{-6}$ M resulted in ~6.9 LacZ units).

EXAMPLE 2

CCRL2 Chemotaxis Assays

Chemotaxis Assay

Figure 6:
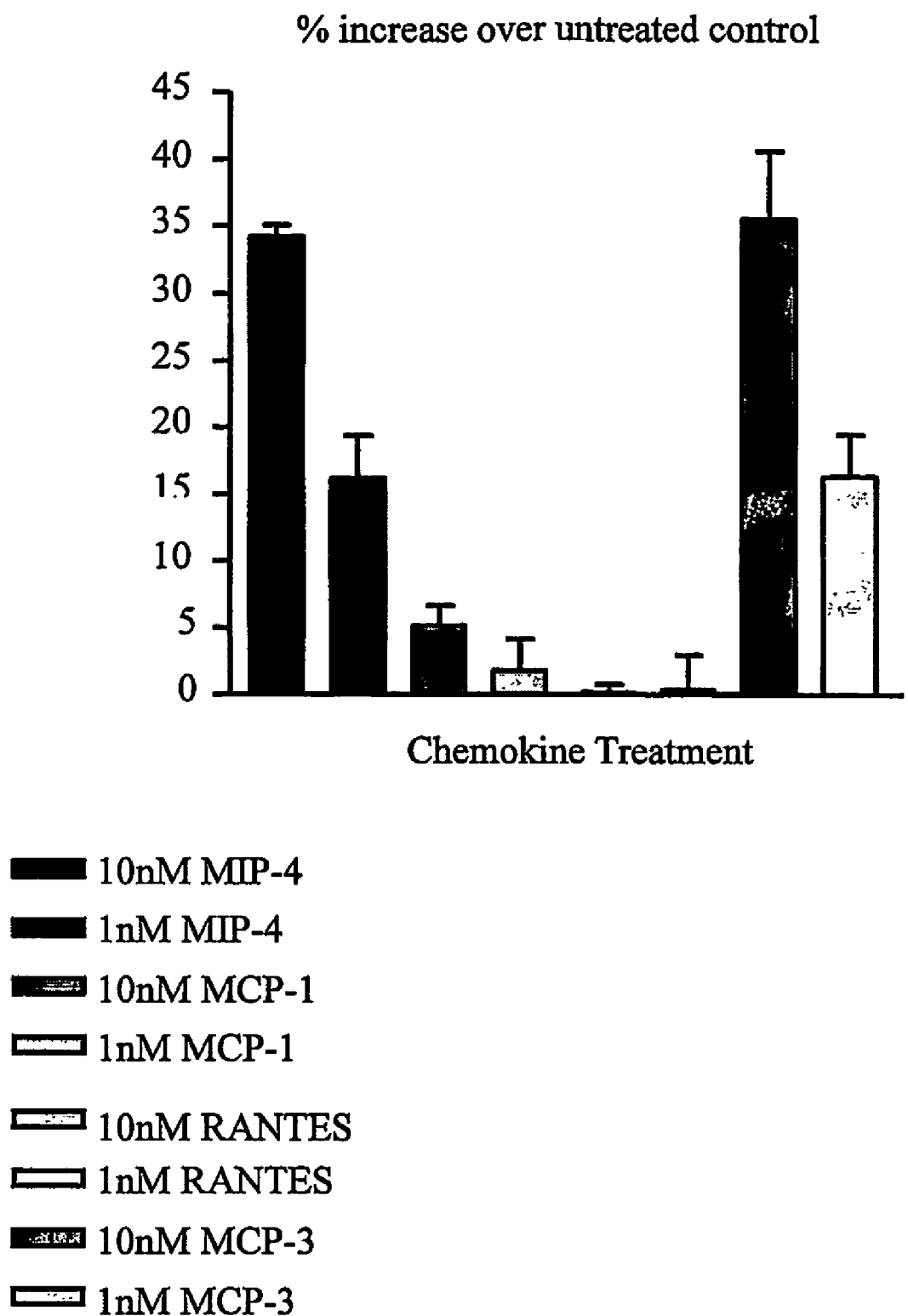
FIG. 6 is a bar graph illustrating the chemotaxis of CCRL2 transfected CHO cells in the presence of various chemokines.

An 8 µm-pore sized 96-well ChemoTx plate (Neuroprobe) was pre-coated with 10 µg/ml fibronectin. Transfected cells were fluorescently-labeled with 5 µg/ml calcein (Molecular Probes) for 30 min at 37° C. 25 µl of cells at a density of $3 \times 10^6$ cells/ml and test samples (29 µl) prepared in appropriate media were applied to the upper and lower chambers of the ChemoTx plate. After incubation at 37° C. for 5 h, any cells remaining on top of the filter were removed by EDTA-treatment and the migrated cells on the underside of the filter and in the wells were quantitated in a fluorescent plate reader (Perkin Elmer). The results are shown in FIG. 6.

MIP-4 stimulated chemotaxis of cells transfected with the short form of CCRL2 (CRAM-B). MIP-4 had no effect on cells that were not transfected with the short form of CCRL2 (CRAM-B).

MCP-1 and MCP-3 which activated the short form of CCRL2 in the yeast assay also showed activity in the chemotaxis assay. A control chemokine, RANTES, which failed to show CCRL2 activation in the yeast assay, did not induce chemotaxis of the CCRL2 transfected cells. 10 nM of both MIP-4 and MCP-3 induced a similar chemotactic activity with approximately 35% more cells passing across the membrane than the untreated cells. The cells only showed a weak chemotactic response in the presence of 10 nM MCP-1.

EXAMPLE 3

AntiCCRL2 Antibody Blocking of MIP-4 Induced Monocyte Chemotaxis

Monocyte Isolation and Culture

Human monocytes were purified (>85%) from buffy coat using an indirect labelling strategy (Monocyte Isolation kit II, Miltenyi Biotech) and cultured for 5 days in RPMI 1640 supplemented with 10% FCS.

Chemotaxis Assay

Cultured monocytes were tested for chemotactic competence using 96-well chemotaxis chambers (HTS Fluroblok™, BD Falcon). Cultured monocytes were pre-labelled with 5 ng/ml Calcein AM (Molecular Probes) for 30 min at 37° C., washed in PBS, then $3 \times 10^4$ cells ($6 \times 10^5$ cells/ml) added to the top chamber. 10 nM of the test chemokine (R&D Systems) was added to the bottom chamber and the chemotaxis plate incubated at room temperature for 10 minutes prior to data collection using a Victor$^2$ fluorometer (Perkin Elmer). All samples were run in triplicate.

Blocking Chemotaxis with Anti-CCRL2 Antibody

Figure 7:
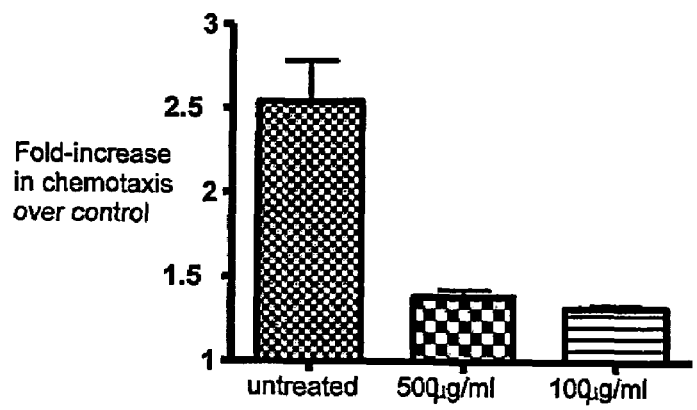
FIG. 7 is a bar graph illustrating the blocking effect of 100 µg/ml and 500 µg/ml anti-CCRL2 antibody on MIP-4 induced chemotaxis.

Anti-CCRL2 antibodies were obtained from R&D Systems. For antibody blocking experiments, Calcein AM labelled monocytes were pre-incubated with varying concentrations of anti-CCRL2 antibodies for 30 minutes at room temperature. Unbound antibody was removed by washing with PBS prior to addition to the chemotaxis plate. Chemotaxis was performed as described above. The results are shown in FIG. 7.

The effect of pre-treatment of cultured monocytes with antibodies against CCRL2 demonstrates that MIP-4 induced chemotaxis of these treated cells is reduced by approximately 75%. As a control, pre-treatment of the cells with an antibody against a chemokine receptor which does not signal via MIP-4 shows no effect on chemotaxis (not shown).

This data shows that the anti-CCRL2 antibody is capable of reducing the chemotactic effect of MIP-4 on cultured monocytes. This confirms that MIP-4 is a ligand for CCRL2 in primary human immune cells.

EXAMPLE 4

Blocking of Synovial Fluid Induced Monocyte Chemotaxis by Anti-CCRL2 Antibody

Monocytes were cultured and isolated as described as above. The chemotaxis plate was set up with monocytes treated or untreated with anti-CCRL2 antibody, again as described above. Synovial fluid was extracted by joint aspiration, centrifuged to remove cells and debris, then aliquoted and frozen until required. Dilutions of synovial fluid were placed in the bottom chamber of the plate and analysed as described above.

Figure 8:
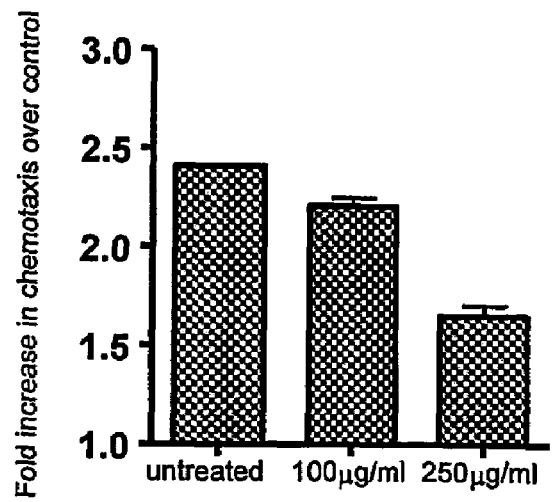
FIG. 8 is a bar graph illustrating the effect of anti-CCRL2 antibodies on RA synovial fluid induced chemotaxis.

The results (shown in FIG. 8) demonstrate that pre-treating cultured monocytes with anti-CCRL2 antibody is able to block chemotaxis induced by diluted (1/100) rheumatoid arthritis (RA) synovial fluid. The highest concentration of antibody tested (250 μg/ml) reduced monocyte chemotaxis by around 50%. This demonstrates that antagonists of CCRL2 would be capable of reducing the chemotaxis of immune cells into inflammatory sites such as Rheumatoid Arthritis and other inflammatory disorders.

EXAMPLE 5

Blocking of RA Synovial Fluid Induced Monocyte Chemotaxis by Anti-MIP-4 Antibody MIP-4 was depleted from RA synovial fluid (RASF) using a method of panning diluted RASF (SF3 1:100) over anti-MIP-4 coated plates. The anti-MIP-4 antibody bound to the plates was purchased from R&D Systems (Cat No. MAB394). These depleted samples were then used to examine the effects this depletion had on RASF induced chemotaxis of cultured monocytes.

Monocytes were cultured and isolated and chemotaxis performed as described above.

Figure 9:
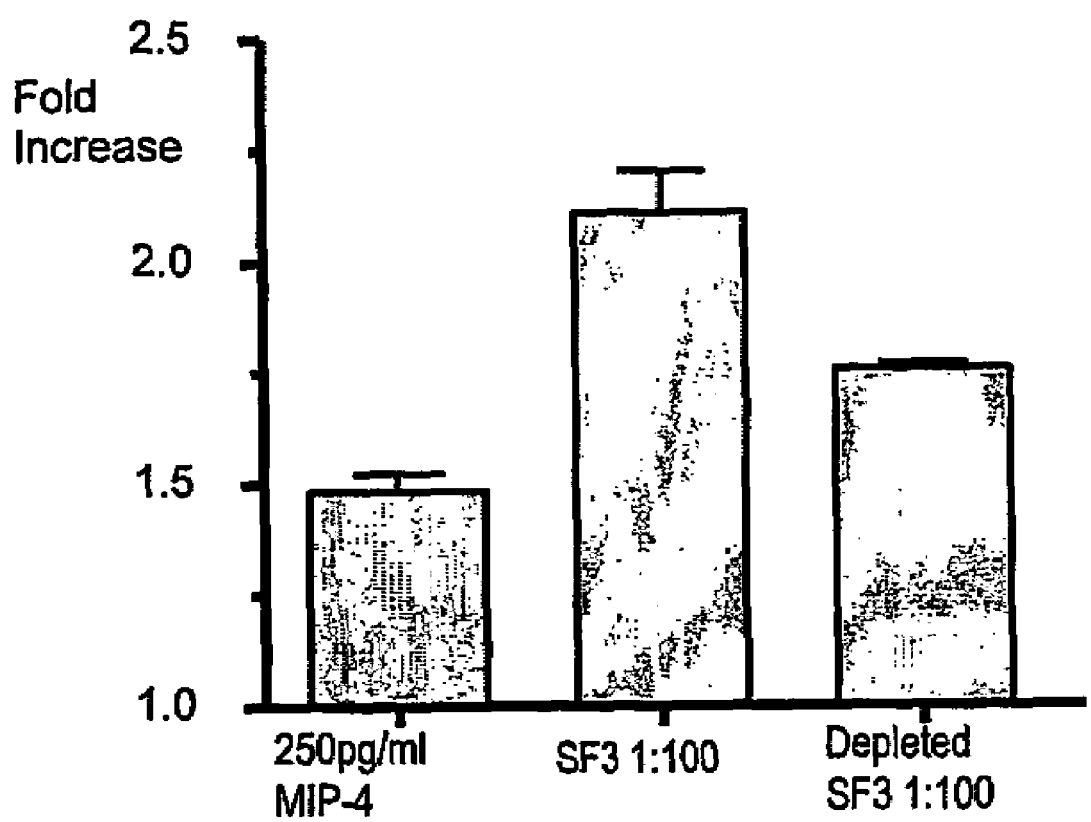
FIG. 9 is a bar graph illustrating the increase in chemotaxis compared to a control observed in response to 250 µg/ml MIP-4, RA synovial fluid (SF3 1:100) and MIP-4 depleted RA synovial fluid (Depleted SF3 1:100).

The procedure to remove MIP-4 did not deplete MIP-4 completely. However, a reduction in the MIP-4 levels was accompanied by a reduction in chemotaxis (Depleted SF3 1:100). Reducing the level of MIP-4 in the diluted RASF by 97% (from 5 ng/ml down to 170 pg/ml) reduced monocyte chemotaxis by around 30%. This is depicted in FIG. 9 below.

The level of MIP-4 (170 pg/ml) remaining in the RASF after depletion was still capable of eliciting a chemotactic response. This is shown in FIG. 9 which demonstrates that 250 pg/ml of rMIP-4 in PBS still gives rise to a 0.5× increase in monocyte chemotaxis.

This data demonstrates that MIP-4 is a major mediator of monocyte induced chemotaxis found in RA synovial fluid. Therefore antibodies specific for MIP-4 have utility in Rheumatoid Arthritis and other inflammatory disorders by reducing the numbers of infiltrating immune cells, both monocyte/macrophages and neutrophils in the case of RA, potentially lessening the symptoms of disease.

The invention claimed is:

1. A method of detecting an agent that modulates the activity of CCRL2, the method comprising:
   (a) contacting a CCRL2 polypeptide comprising the sequence shown in SEQ ID NO: 2 or 4 with a macrophage inflammatory protein-4 (MIP-4) polypeptide comprising the sequence shown in SEQ ID NO: 6 in the presence of a candidate agent under conditions, which in the absence of the candidate agent, permit the binding of the MIP-4 polypeptide to the CCRL2 polypeptide; and
   (b) monitoring binding of the CCRL2 polypeptide to MIP-4 polypeptide or activity of the CCRL2 polypeptide,
   wherein if there is a difference between the amount of binding or activity in the absence of the candidate agent and in the presence of it, then said agent is identified as a modulating agent.

2. A method according to claim 1, wherein the candidate agent is a polypeptide, an antibody or antigen-binding fragment thereof, a lipid, a carbohydrate, a nucleic acid or a chemical compound.

3. A method according to claim 1, wherein step (b) comprises monitoring binding of the CCRL2 polypeptide to the MIP-4 polypeptide.

4. A method according to claim 3, wherein the binding of the CCRL2 polypeptide to the MIP-4 polypeptide is monitored using label displacement, surface plasmon resonance, fluorescence resonance energy transfer, fluorescence quenching or fluorescence polarization.

5. A method according to claim 1, wherein the MIP-4 polypeptide is detectably labelled.

6. A method according to claim 5, wherein the MIP-4 polypeptide is detectably labelled with a moiety is a radioisotope, a fluorophore, a quencher of fluorescence, an enzyme, an affinity tag or an epitope tag.

7. A method according to claim 1, wherein step (b) comprises monitoring the signalling activity of the CCRL2 polypeptide.

8. A method according to claim 7, wherein the signalling activity is monitored by measurement of guanosine nucleotide binding, GTPase activity, adenylate cyclase activity, cyclic adenosine monophosphate (cAMP), Protein Kinase C activity, phosphatidylinositol breakdown, diacylglycerol, inositol triphosphate, intracellular calcium, MAP kinase activity or reporter gene expression.

9. A method according to claim 8, wherein the signalling activity is monitored by measuring the activity of Gi3.

10. A method according to claim 1, wherein step (b) comprises monitoring the chemotactic activity of the CCRL2 polypeptide.

11. A method according to claim 1, wherein the CCRL2 polypeptide is expressed on a cell.

12. A method according to claim 11, wherein the cell is a yeast cell.

13. A method according to claim 12, wherein the yeast cell comprises a G protein in which at least 5 amino acids at the carboxy terminal of a yeast G subunit have been replaced with the corresponding residues from a non-yeast G protein.

14. A method according to claim 13, wherein the non-yeast G-protein is Gi3.

15. A method according to claim 1, wherein the CCRL2 polypeptide is present:
   (a) in or on synthetic liposomes; or
   (b) in or on virus-induced budding membranes; or
   (c) in or on an artificial lipid bilayer; or
   (d) in a membrane fraction from cells expressing the CCRL2 polypeptide.

16. A kit for detecting an agent that modulates the activity of CCRL2 as in claim 1, the kit comprising: (i) a MIP-4 polypeptide comprising the sequence shown in SEQ ID NO: 6; and (ii) a CCRL2 polypeptide comprising the sequence shown in SEQ ID NO: 2 or 4 or a polynucleotide encoding a CCRL2 polypeptide comprising the sequence shown SEQ ID NO: 2 or 4, where (i) and (ii) are in separate containers.

17. A kit according to claim 16, which comprises a cell transformed with a polynucleotide encoding a CCRL2 polypeptide.

18. A kit according to claim 16, wherein the CCRL2 polypeptide is present in a cell membrane fraction, a synthetic liposome or a virus-induced budding membrane.

19. A method of detecting an agent that modulates the activity of CCRL2, the method comprising:
(a) contacting a CCRL2 polypeptide comprising:
the sequence shown in SEQ ID NO: 2 or 4, or
a sequence which is at least 90% identical to the sequence shown in SEQ ID NO: 2 or 4 over its entire length and which has the receptor activity of CCRL2;
with a macrophage inflammatory protein-4 (MIP-4) polypeptide comprising
the sequence shown in SEQ ID NO: 6, or
a sequence which is at least 90% identical to the sequence shown in SEQ ID NO: 6 over its entire length and which binds to and activates a signalling activity of CCRL2;
where the CCRL2 polypeptide and MIP-4 polypeptide are contacted in the presence of a candidate agent under conditions, which in the absence of the candidate agent, permit the binding of the MIP-4 polypeptide to the CCRL2 polypeptide; and
(b) monitoring binding of the CCRL2 polypeptide to the MIP-4 polypeptide or activity of the CCRL2 polypeptide,
wherein if there is a difference between the amount of binding or activity in the absence of the candidate agent and in the presence of it, then said agent is identified as a modulating agent.

* * * * *

SEQUENCE LISTING

```
<160> NUMBER OF SEQ ID NOS: 6

<210> SEQ ID NO 1
<211> LENGTH: 1531
<212> TYPE: DNA
<213> ORGANISM: Homo sapiens
<220> FEATURE:
<221> NAME/KEY: CDS
<222> LOCATION: (48)..(1118)

<400> SEQUENCE: 1
aggaagctgc ttcgggggt gagcaaactt tttaaaatgc agaaatt atg atc tac      56
                                                   Met Ile Tyr
                                                    1 acc cgt ttc tta aaa ggc agt ctg aag atg gcc aat tac acg ctg gca   104
Thr Arg Phe Leu Lys Gly Ser Leu Lys Met Ala Asn Tyr Thr Leu Ala
      5                  10                  15 cca gag gat gaa tat gat gtc ctc ata gaa ggt gaa ctg gag agc gat   152
Pro Glu Asp Glu Tyr Asp Val Leu Ile Glu Gly Glu Leu Glu Ser Asp
 20                  25                  30                  35 gag gca gag caa tgt gac aag tat gac gcc cag gca ctc tca gcc cag   200
Glu Ala Glu Gln Cys Asp Lys Tyr Asp Ala Gln Ala Leu Ser Ala Gln
                 40                  45                  50 ctg gtg cca tca ctc tgc tct gct gtg ttt gtg atc ggt gtc ctg gac   248
Leu Val Pro Ser Leu Cys Ser Ala Val Phe Val Ile Gly Val Leu Asp
             55                  60                  65 aat ctc ctg gtt gtg ctt atc ctg gta aaa tat aaa gga ctc aaa cgc   296
Asn Leu Leu Val Val Leu Ile Leu Val Lys Tyr Lys Gly Leu Lys Arg
         70                  75                  80 gtg gaa aat atc tat ctt cta aac ttg gca gtt tct aac ttg tgt ttc   344
Val Glu Asn Ile Tyr Leu Leu Asn Leu Ala Val Ser Asn Leu Cys Phe
     85                  90                  95 ttg ctt acc ctg ccc ttc tgg gct cat gct ggg ggc gat ccc atg tgt   392
Leu Leu Thr Leu Pro Phe Trp Ala His Ala Gly Gly Asp Pro Met Cys
100                 105                 110                 115 aaa att ctc att gga ctg tac ttc gtg ggc ctg tac agt gag aca ttt   440
Lys Ile Leu Ile Gly Leu Tyr Phe Val Gly Leu Tyr Ser Glu Thr Phe
```

-continued

```
                    120                 125                 130
ttc aat tgc ctt ctg act gtg caa agg tac cta gtg ttt ttg cac aag      488
Phe Asn Cys Leu Leu Thr Val Gln Arg Tyr Leu Val Phe Leu His Lys
                135                 140                 145 ggc aac ttt ttc tca gcc agg agg agg gtg ccc tgt ggc atc att aca      536
Gly Asn Phe Phe Ser Ala Arg Arg Arg Val Pro Cys Gly Ile Ile Thr
            150                 155                 160 agt gtc ctg gca tgg gta aca gcc att ctg gcc act ttg cct gaa tac      584
Ser Val Leu Ala Trp Val Thr Ala Ile Leu Ala Thr Leu Pro Glu Tyr
        165                 170                 175 gtg gtt tat aaa cct cag atg gaa gac cag aaa tac aag tgt gca ttt      632
Val Val Tyr Lys Pro Gln Met Glu Asp Gln Lys Tyr Lys Cys Ala Phe
    180                 185                 190                 195 agc aga act ccc ttc ctg cca gct gat gag aca ttc tgg aag cat ttt      680
Ser Arg Thr Pro Phe Leu Pro Ala Asp Glu Thr Phe Trp Lys His Phe
                200                 205                 210 ctg act tta aaa atg aac att tcg gtt ctt gtc ctc ccc cta ttt att      728
Leu Thr Leu Lys Met Asn Ile Ser Val Leu Val Leu Pro Leu Phe Ile
            215                 220                 225 ttt aca ttt ctc tat gtg caa atg aga aaa aca cta agg ttc agg gag      776
Phe Thr Phe Leu Tyr Val Gln Met Arg Lys Thr Leu Arg Phe Arg Glu
        230                 235                 240 cag agg tat agc ctt ttc aag ctt gtt ttt gcc ata atg gta gtc ttc      824
Gln Arg Tyr Ser Leu Phe Lys Leu Val Phe Ala Ile Met Val Val Phe
    245                 250                 255 ctt ctg atg tgg gcg ccc tac aat att gca ttt ttc ctg tcc act ttc      872
Leu Leu Met Trp Ala Pro Tyr Asn Ile Ala Phe Phe Leu Ser Thr Phe
260                 265                 270                 275 aaa gaa cac ttc tcc ctg agt gac tgc aag agc agc tac aat ctg gac      920
Lys Glu His Phe Ser Leu Ser Asp Cys Lys Ser Ser Tyr Asn Leu Asp
                280                 285                 290 aaa agt gtt cac atc act aaa ctc atc gcc acc acc cac tgc tgc atc      968
Lys Ser Val His Ile Thr Lys Leu Ile Ala Thr Thr His Cys Cys Ile
            295                 300                 305 aac cct ctc ctg tat gcg ttt ctt gat ggg aca ttt agc aaa tac ctc     1016
Asn Pro Leu Leu Tyr Ala Phe Leu Asp Gly Thr Phe Ser Lys Tyr Leu
        310                 315                 320 tgc cgc tgt ttc cat ctg cgt agt aac acc cca ctt caa ccc agg ggg     1064
Cys Arg Cys Phe His Leu Arg Ser Asn Thr Pro Leu Gln Pro Arg Gly
    325                 330                 335 cag tct gca caa ggc aca tcg agg gaa gaa cct gac cat tcc acc gaa     1112
Gln Ser Ala Gln Gly Thr Ser Arg Glu Glu Pro Asp His Ser Thr Glu
340                 345                 350                 355 gtg taa actagcatcc accaaatgca agaagaataa acatggattt tcatctttct      1168
Val gcattatttc atgtaaattt tctacacatt tgtatacaaa atcggataca ggaagaaaag   1228
ggagaggtga gctaacattt gctaagcact gaatttgtct caggcaccgt gcaaggctct   1288
ttacaaacgt gagctccttc gcctcctacc acttgtccat agtgtggata ggactagtct   1348
catttctctg agaagaaaac taaggcgcgg aaatttgtct aagatcacat aactaggaag   1408
tggcagaact gattctccag ccctggtagc atttgctcag agcctacgct tggtccagaa   1468
catcaaactc caaaccctgg ggacaaacga catgaaataa atgtatttta aaacatctaa   1528
aaa                                                                1531
```

<210> SEQ ID NO 2
<211> LENGTH: 356
<212> TYPE: PRT

<213> ORGANISM: Homo sapiens

<400> SEQUENCE: 2

```
Met Ile Tyr Thr Arg Phe Leu Lys Gly Ser Leu Lys Met Ala Asn Tyr
1               5                   10                  15

Thr Leu Ala Pro Glu Asp Glu Tyr Asp Val Leu Ile Glu Gly Glu Leu
            20                  25                  30

Glu Ser Asp Glu Ala Glu Gln Cys Asp Lys Tyr Asp Ala Gln Ala Leu
        35                  40                  45

Ser Ala Gln Leu Val Pro Ser Leu Cys Ser Ala Val Phe Val Ile Gly
50                  55                  60

Val Leu Asp Asn Leu Leu Val Leu Ile Leu Val Lys Tyr Lys Gly
65                  70                  75                  80

Leu Lys Arg Val Glu Asn Ile Tyr Leu Leu Asn Leu Ala Val Ser Asn
                85                  90                  95

Leu Cys Phe Leu Leu Thr Leu Pro Phe Trp Ala His Ala Gly Gly Asp
            100                 105                 110

Pro Met Cys Lys Ile Leu Ile Gly Leu Tyr Phe Val Gly Leu Tyr Ser
        115                 120                 125

Glu Thr Phe Phe Asn Cys Leu Leu Thr Val Gln Arg Tyr Leu Val Phe
130                 135                 140

Leu His Lys Gly Asn Phe Phe Ser Ala Arg Arg Val Pro Cys Gly
145                 150                 155                 160

Ile Ile Thr Ser Val Leu Ala Trp Val Thr Ala Ile Leu Ala Thr Leu
                165                 170                 175

Pro Glu Tyr Val Val Tyr Lys Pro Gln Met Glu Asp Gln Lys Tyr Lys
            180                 185                 190

Cys Ala Phe Ser Arg Thr Pro Phe Leu Pro Ala Asp Glu Thr Phe Trp
        195                 200                 205

Lys His Phe Leu Thr Leu Lys Met Asn Ile Ser Val Leu Val Leu Pro
210                 215                 220

Leu Phe Ile Phe Thr Phe Leu Tyr Val Gln Met Arg Lys Thr Leu Arg
225                 230                 235                 240

Phe Arg Glu Gln Arg Tyr Ser Leu Phe Lys Leu Val Phe Ala Ile Met
                245                 250                 255

Val Val Phe Leu Leu Met Trp Ala Pro Tyr Asn Ile Ala Phe Phe Leu
            260                 265                 270

Ser Thr Phe Lys Glu His Phe Ser Leu Ser Asp Cys Lys Ser Ser Tyr
        275                 280                 285

Asn Leu Asp Lys Ser Val His Ile Thr Lys Leu Ile Ala Thr Thr His
290                 295                 300

Cys Cys Ile Asn Pro Leu Leu Tyr Ala Phe Leu Asp Gly Thr Phe Ser
305                 310                 315                 320

Lys Tyr Leu Cys Arg Cys Phe His Leu Arg Ser Asn Thr Pro Leu Gln
                325                 330                 335

Pro Arg Gly Gln Ser Ala Gln Gly Thr Ser Arg Glu Glu Pro Asp His
            340                 345                 350

Ser Thr Glu Val
        355
```

<210> SEQ ID NO 3
<211> LENGTH: 1771
<212> TYPE: DNA
<213> ORGANISM: Homo sapiens
<220> FEATURE:

```
<221> NAME/KEY: CDS
<222> LOCATION: (328)..(1362)

<400> SEQUENCE: 3
aaaggtcaca gggaaatcaa aggcggggta cagggccaga gggaggagga aacaacttcc      60
cggttgcttt cagacgcttc agagatcctc tggaggcctg ggggagcttt tgagtacttt     120
atttcagttg gtccctgagc tcggtgagtg gggcgggtag agccaccagg ggaatcaaca     180
gtggtttctc gtgcccctca gggtcaggag cagtctgatc aaaaggaggg catccactgt     240
ccggggccat tcccacagct cccggatgct gggtctggag gctgcgccct tcccctgcag     300
gagctcagcc cagtgggcag tctgaag atg gcc aat tac acg ctg gca cca gag     354
                               Met Ala Asn Tyr Thr Leu Ala Pro Glu
                                 1               5 gat gaa tat gat gtc ctc ata gaa ggt gaa ctg gag agc gat gag gca       402
Asp Glu Tyr Asp Val Leu Ile Glu Gly Glu Leu Glu Ser Asp Glu Ala
 10              15                  20                  25 gag caa tgt gac aag tat gac gcc cag gca ctc tca gcc cag ctg gtg       450
Glu Gln Cys Asp Lys Tyr Asp Ala Gln Ala Leu Ser Ala Gln Leu Val
                 30                  35                  40 cca tca ctc tgc tct gct gtg ttt gtg atc ggt gtc ctg gac aat ctc       498
Pro Ser Leu Cys Ser Ala Val Phe Val Ile Gly Val Leu Asp Asn Leu
             45                  50                  55 ctg gtt gtg ctt atc ctg gta aaa tat aaa gga ctc aaa cgc gtg gaa       546
Leu Val Val Leu Ile Leu Val Lys Tyr Lys Gly Leu Lys Arg Val Glu
         60                  65                  70 aat atc tat ctt cta aac ttg gca gtt tct aac ttg tgt ttc ttg ctt       594
Asn Ile Tyr Leu Leu Asn Leu Ala Val Ser Asn Leu Cys Phe Leu Leu
 75                  80                  85 acc ctg ccc ttc tgg gct cat gct ggg ggc gat ccc atg tgt aaa att       642
Thr Leu Pro Phe Trp Ala His Ala Gly Gly Asp Pro Met Cys Lys Ile
 90                  95                 100                 105 ctc att gga ctg tac ttc gtg ggc ctg tac agt gag aca ttt ttc aat       690
Leu Ile Gly Leu Tyr Phe Val Gly Leu Tyr Ser Glu Thr Phe Phe Asn
                110                 115                 120 tgc ctt ctg act gtg caa agg tac cta gtg ttt ttg cac aag ggc aac       738
Cys Leu Leu Thr Val Gln Arg Tyr Leu Val Phe Leu His Lys Gly Asn
            125                 130                 135 ttt ttc tca gcc agg agg agg gtg ccc tgt ggc atc att aca agt gtc       786
Phe Phe Ser Ala Arg Arg Arg Val Pro Cys Gly Ile Ile Thr Ser Val
        140                 145                 150 ctg gca tgg gta aca gcc att ctg gcc act ttg cct gaa tac gtg gtt       834
Leu Ala Trp Val Thr Ala Ile Leu Ala Thr Leu Pro Glu Tyr Val Val
    155                 160                 165 tat aaa cct cag atg gaa gac cag aaa tac aag tgt gca ttt agc aga       882
Tyr Lys Pro Gln Met Glu Asp Gln Lys Tyr Lys Cys Ala Phe Ser Arg
170                 175                 180                 185 act ccc ttc ctg cca gct gat gag aca ttc tgg aag cat ttt ctg act       930
Thr Pro Phe Leu Pro Ala Asp Glu Thr Phe Trp Lys His Phe Leu Thr
                190                 195                 200 tta aaa atg aac att tcg gtt ctt gtc ctc ccc cta ttt att ttt aca       978
Leu Lys Met Asn Ile Ser Val Leu Val Leu Pro Leu Phe Ile Phe Thr
            205                 210                 215 ttt ctc tat gtg caa atg aga aaa aca cta agg ttc agg gag cag agg      1026
Phe Leu Tyr Val Gln Met Arg Lys Thr Leu Arg Phe Arg Glu Gln Arg
        220                 225                 230 tat agc ctt ttc aag ctt gtt ttt gcc ata atg gta gtc ttc ctt ctg      1074
Tyr Ser Leu Phe Lys Leu Val Phe Ala Ile Met Val Val Phe Leu Leu
    235                 240                 245
```

```
atg tgg gcg ccc tac aat att gca ttt ttc ctg tcc act ttc aaa gaa    1122
Met Trp Ala Pro Tyr Asn Ile Ala Phe Phe Leu Ser Thr Phe Lys Glu
250                 255                 260                 265 cac ttc tcc ctg agt gac tgc aag agc agc tac aat ctg gac aaa agt    1170
His Phe Ser Leu Ser Asp Cys Lys Ser Ser Tyr Asn Leu Asp Lys Ser
                270                 275                 280 gtt cac atc act aaa ctc atc gcc acc acc cac tgc tgc atc aac cct    1218
Val His Ile Thr Lys Leu Ile Ala Thr Thr His Cys Cys Ile Asn Pro
            285                 290                 295 ctc ctg tat gcg ttt ctt gat ggg aca ttt agc aaa tac ctc tgc cgc    1266
Leu Leu Tyr Ala Phe Leu Asp Gly Thr Phe Ser Lys Tyr Leu Cys Arg
        300                 305                 310 tgt ttc cat ctg cgt agt aac acc cca ctt caa ccc agg ggg cag tct    1314
Cys Phe His Leu Arg Ser Asn Thr Pro Leu Gln Pro Arg Gly Gln Ser
    315                 320                 325 gca caa ggc aca tcg agg gaa gaa cct gac cat tcc acc gaa gtg taa    1362
Ala Gln Gly Thr Ser Arg Glu Glu Pro Asp His Ser Thr Glu Val
330                 335                 340 actagcatcc accaaatgca agaagaataa acatggattt tcatctttct gcattatttc    1422
atgtaaattt tctacacatt tgtatacaaa atcggataca ggaagaaaag ggagaggtga    1482
gctaacattt gctaagcact gaatttgtct caggcaccgt gcaaggctct ttacaaacgt    1542
gagctccttc gcctcctacc acttgtccat agtgtggata ggactagtct caattctctg    1602
agaagaaaac taaggcgcgg aaatttgtct aagatcacat aactaggaag tggcagaact    1662
gattctccag ccctggtagc atttgctcag agcctacgct tggtccagaa catcaaactc    1722
caaaccctgg ggacaaacga catgaaataa atgtatttta aaacatcta              1771

<210> SEQ ID NO 4
<211> LENGTH: 344
<212> TYPE: PRT
<213> ORGANISM: Homo sapiens

<400> SEQUENCE: 4

Met Ala Asn Tyr Thr Leu Ala Pro Glu Asp Glu Tyr Asp Val Leu Ile
1               5                   10                  15

Glu Gly Glu Leu Glu Ser Asp Glu Ala Glu Gln Cys Asp Lys Tyr Asp
            20                  25                  30

Ala Gln Ala Leu Ser Ala Gln Leu Val Pro Ser Leu Cys Ser Ala Val
        35                  40                  45

Phe Val Ile Gly Val Leu Asp Asn Leu Leu Val Leu Ile Leu Val
    50                  55                  60

Lys Tyr Lys Gly Leu Lys Arg Val Glu Asn Ile Tyr Leu Leu Asn Leu
65                  70                  75                  80

Ala Val Ser Asn Leu Cys Phe Leu Leu Thr Leu Pro Phe Trp Ala His
                85                  90                  95

Ala Gly Gly Asp Pro Met Cys Lys Ile Leu Ile Gly Leu Tyr Phe Val
            100                 105                 110

Gly Leu Tyr Ser Glu Thr Phe Phe Asn Cys Leu Leu Thr Val Gln Arg
        115                 120                 125

Tyr Leu Val Phe Leu His Lys Gly Asn Phe Phe Ser Ala Arg Arg Arg
    130                 135                 140

Val Pro Cys Gly Ile Ile Thr Ser Val Leu Ala Trp Val Thr Ala Ile
145                 150                 155                 160

Leu Ala Thr Leu Pro Glu Tyr Val Val Tyr Lys Pro Gln Met Glu Asp
                165                 170                 175
```

```
Gln Lys Tyr Lys Cys Ala Phe Ser Arg Thr Pro Phe Leu Pro Ala Asp
            180                 185                 190
Glu Thr Phe Trp Lys His Phe Leu Thr Leu Lys Met Asn Ile Ser Val
            195                 200                 205
Leu Val Leu Pro Leu Phe Ile Phe Thr Phe Leu Tyr Val Gln Met Arg
            210                 215                 220
Lys Thr Leu Arg Phe Arg Glu Gln Arg Tyr Ser Leu Phe Lys Leu Val
225                 230                 235                 240
Phe Ala Ile Met Val Val Phe Leu Leu Met Trp Ala Pro Tyr Asn Ile
                245                 250                 255
Ala Phe Phe Leu Ser Thr Phe Lys Glu His Phe Ser Leu Ser Asp Cys
            260                 265                 270
Lys Ser Ser Tyr Asn Leu Asp Lys Ser Val His Ile Thr Lys Leu Ile
            275                 280                 285
Ala Thr Thr His Cys Cys Ile Asn Pro Leu Leu Tyr Ala Phe Leu Asp
            290                 295                 300
Gly Thr Phe Ser Lys Tyr Leu Cys Arg Cys Phe His Leu Arg Ser Asn
305                 310                 315                 320
Thr Pro Leu Gln Pro Arg Gly Gln Ser Ala Gln Gly Ser Thr Ser Arg Glu
            325                 330                 335
Glu Pro Asp His Ser Thr Glu Val
            340
```

<210> SEQ ID NO 5
<211> LENGTH: 793
<212> TYPE: DNA
<213> ORGANISM: Homo sapiens
<220> FEATURE:
<221> NAME/KEY: CDS
<222> LOCATION: (61)..(330)

<400> SEQUENCE: 5

```
aggagttgtg agtttccaag ccccagctca ctctgaccac ttctctgcct gcccagcatc    60 atg aag ggc ctt gca gct gcc ctc ctt gtc ctc gtc tgc acc atg gcc    108
Met Lys Gly Leu Ala Ala Ala Leu Leu Val Leu Val Cys Thr Met Ala
1               5                   10                  15 ctc tgc tcc tgt gca caa gtt ggt acc aac aaa gag ctc tgc tgc ctc    156
Leu Cys Ser Cys Ala Gln Val Gly Thr Asn Lys Glu Leu Cys Cys Leu
            20                  25                  30 gtc tat acc tcc tgg cag att cca caa aag ttc ata gtt gac tat tct    204
Val Tyr Thr Ser Trp Gln Ile Pro Gln Lys Phe Ile Val Asp Tyr Ser
        35                  40                  45 gaa acc agc ccc cag tgc ccc aag cca ggt gtc atc ctc cta acc aag    252
Glu Thr Ser Pro Gln Cys Pro Lys Pro Gly Val Ile Leu Leu Thr Lys
    50                  55                  60 aga ggc cgg cag atc tgt gct gac ccc aat aag aag tgg gtc cag aaa    300
Arg Gly Arg Gln Ile Cys Ala Asp Pro Asn Lys Lys Trp Val Gln Lys
65                  70                  75                  80 tac atc agc gac ctg aag ctg aat gcc tga ggggcctgga agctgcgagg       350
Tyr Ile Ser Asp Leu Lys Leu Asn Ala
                85 gcccagtgaa cttggtgggc caggaggga acaggagcct gagccagggc aatggccctg    410 ccaccctgga ggccacctct tctaagagtc ccatctgcta tgcccagcca cattaactaa    470 ctttaatctt agtttatgca tcatatttca ttttgaaatt gatttctatt gttgagctgc    530 attatgaaat tagtattttc tctgacatct catgacattg tctttatcat cctttccct    590 ttcccttcaa ctcttcgtac attcaatgca tggatcaatc agtgtgatta gctttctcag    650
```

```
                                          -continued cagacattgt gccatatgta tcaaatgaca aatctttatt gaatggtttt gctcagcacc       710
accttttaat atattggcag tacttattat ataaaaggta aaccagcatt ctcactgtga       770
aaaaaaaaaa aaaaaaaaaa aaa                                              793

<210> SEQ ID NO 6
<211> LENGTH: 89
<212> TYPE: PRT
<213> ORGANISM: Homo sapiens

<400> SEQUENCE: 6

Met Lys Gly Leu Ala Ala Ala Leu Leu Val Leu Val Cys Thr Met Ala
1               5                  10                  15

Leu Cys Ser Cys Ala Gln Val Gly Thr Asn Lys Glu Leu Cys Cys Leu
            20                  25                  30

Val Tyr Thr Ser Trp Gln Ile Pro Gln Lys Phe Ile Val Asp Tyr Ser
        35                  40                  45

Glu Thr Ser Pro Gln Cys Pro Lys Pro Gly Val Ile Leu Leu Thr Lys
    50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85
```